United States Patent
Al-Ali et al.

(10) Patent No.: US 10,912,524 B2
(45) Date of Patent: Feb. 9, 2021

(54) MODULAR PATIENT MONITOR

(71) Applicant: MASIMO CORPORATION, Irvine, CA (US)

(72) Inventors: Ammar Al-Ali, San Juan Capistrano, CA (US); Paul Jansen, San Clemente, CA (US); Massi Joe E. Kiani, Laguna Niguel, CA (US); Anand Sampath, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 1275 days.

(21) Appl. No.: 14/464,560

(22) Filed: Aug. 20, 2014

(65) Prior Publication Data

US 2014/0357966 A1 Dec. 4, 2014

Related U.S. Application Data

(63) Continuation of application No. 11/903,746, filed on Sep. 24, 2007, now Pat. No. 8,840,549.

(Continued)

(51) Int. Cl.
*A61B 5/00* (2006.01)
*A61B 5/0205* (2006.01)
(Continued)

(52) U.S. Cl.
CPC .......... *A61B 5/7445* (2013.01); *A61B 5/0002* (2013.01); *A61B 5/0205* (2013.01);
(Continued)

(58) Field of Classification Search
CPC ....... A61B 5/742; A61B 5/743; A61B 5/7475; A61B 5/7445; A61B 5/6898;
(Continued)

(56) References Cited

U.S. PATENT DOCUMENTS 3,646,606 A 2/1972 Buxton et al.
3,690,313 A 9/1972 Weber et al.
(Continued)

FOREIGN PATENT DOCUMENTS

EP 735499 10/1996
EP 1 110 503 6/2001
(Continued)

OTHER PUBLICATIONS

US 8,845,543 B2, 09/2014, Diab et al. (withdrawn)
(Continued)

*Primary Examiner* — Niketa I Patel
*Assistant Examiner* — Nathan A Baldwin
(74) *Attorney, Agent, or Firm* — Knobbe Martens Olson & Bear LLP

(57) ABSTRACT

A modular patient monitor has a docking station configured to accept a handheld monitor. The docking station has standalone patient monitoring functionality with respect to a first set of parameters. At least some of the first parameter set are displayed simultaneously on a full-sized screen integrated with the docking station. The handheld monitor also has standalone patient monitoring functionality with respect to a second set of parameters. At least some of the second set of parameters are displayed simultaneously on a handheld-sized screen integrated with the handheld monitor. The docking station has a port configured to accept the handheld monitor. While the handheld monitor is docket in the port, the docking station functionally combines the first set of parameters and the second set of parameters, and at least some of the combined first and second sets of parameters are displayed simultaneously on the full-sized screen.

18 Claims, 17 Drawing Sheets

Related U.S. Application Data

(60) Provisional application No. 60/846,471, filed on Sep. 22, 2006.

(51) Int. Cl.
*A61B 5/0402* (2006.01)
*A61B 5/145* (2006.01)
*A61B 5/1455* (2006.01)
*A61B 5/1464* (2006.01)
*A61B 5/021* (2006.01)
*A61B 5/024* (2006.01)

(52) U.S. Cl.
CPC .......... *A61B 5/0402* (2013.01); *A61B 5/1464* (2013.01); *A61B 5/14532* (2013.01); *A61B 5/14546* (2013.01); *A61B 5/14551* (2013.01); *A61B 5/6887* (2013.01); *A61B 5/7282* (2013.01); *A61B 5/742* (2013.01); *A61B 5/021* (2013.01); *A61B 5/024* (2013.01); *A61B 5/1455* (2013.01); *A61B 2560/0456* (2013.01)

(58) Field of Classification Search
CPC ...... A61B 2560/045; A61B 2560/0443; A61B 2560/0456
See application file for complete search history.

(56) References Cited

U.S. PATENT DOCUMENTS

| | | |
|---|---|---|
| 3,810,102 A | 5/1974 | Parks, III et al. |
| 3,815,583 A | 6/1974 | Scheidt |
| 3,972,320 A | 8/1976 | Kalman |
| 3,978,849 A | 9/1976 | Geneen |
| 4,108,166 A | 8/1978 | Schmid |
| 4,231,354 A | 11/1980 | Kurtz et al. |
| 4,589,415 A | 5/1986 | Haaga |
| 4,662,378 A | 5/1987 | Thomis |
| 4,838,275 A | 6/1989 | Lee |
| 4,852,570 A | 8/1989 | Levine |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,296,688 A | 3/1994 | Hamilton et al. |
| 5,309,918 A | 5/1994 | Schraag |
| 5,318,037 A | 6/1994 | Evans et al. |
| 5,319,355 A | 6/1994 | Russek |
| 5,331,549 A | 7/1994 | Crawford, Jr. |
| 5,333,106 A | 7/1994 | Lanpher et al. |
| 5,337,744 A | 8/1994 | Branigan |
| 5,341,805 A | 8/1994 | Stavridi et al. |
| 5,348,008 A | 9/1994 | Bornn et al. |
| 5,358,519 A | 10/1994 | Grandjean |
| D353,195 S | 12/1994 | Savage et al. |
| D353,196 S | 12/1994 | Savage et al. |
| 5,375,599 A | 12/1994 | Schimizu |
| 5,375,604 A | 12/1994 | Kelly et al. |
| 5,377,676 A | 1/1995 | Vari et al. |
| 5,400,794 A | 3/1995 | Gorman |
| 5,406,952 A | 4/1995 | Barnes et al. |
| D357,982 S | 5/1995 | Dahl et al. |
| 5,416,695 A | 5/1995 | Stutman et al. |
| D359,546 S | 6/1995 | Savage et al. |
| 5,431,170 A | 7/1995 | Mathews |
| 5,434,611 A | 7/1995 | Tamura |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,533,511 A | 7/1996 | Kaspari et al. |
| 5,534,851 A | 7/1996 | Russek |
| 5,537,289 A | 7/1996 | Dahl |
| 5,544,649 A | 8/1996 | David et al. |
| 5,553,609 A | 9/1996 | Chen et al. |
| 5,558,638 A * | 9/1996 | Evers ................... A61B 5/0444 604/66 |
| 5,561,275 A | 10/1996 | Savage et al. |
| 5,562,002 A | 10/1996 | Lalin |
| 5,566,676 A | 10/1996 | Rosenfeldt et al. |
| 5,576,952 A | 11/1996 | Stutman et al. |
| 5,579,001 A | 11/1996 | Dempsey et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,953 A | 6/1997 | Bishop et al. |
| 5,640,967 A | 6/1997 | Fine et al. |
| 5,645,440 A | 7/1997 | Tobler et al. |
| 5,671,914 A | 9/1997 | Kalkhoran et al. |
| 5,685,299 A | 11/1997 | Diab et al. |
| 5,685,314 A | 11/1997 | Geheb et al. |
| 5,687,717 A | 11/1997 | Halpern et al. |
| 5,694,020 A | 12/1997 | Lang |
| 5,724,580 A | 3/1998 | Levin et al. |
| 5,724,983 A | 3/1998 | Selker et al. |
| 5,725,308 A | 3/1998 | Smith et al. |
| 5,726,440 A | 3/1998 | Kalkhoran et al. |
| 5,734,739 A | 3/1998 | Sheehan et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,079 A | 5/1998 | Ludwig et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,585 A | 6/1998 | Lavin et al. |
| 5,782,757 A | 7/1998 | Diab et al. |
| 5,782,805 A | 7/1998 | Meinzer |
| 5,785,659 A | 7/1998 | Caro et al. |
| 5,791,347 A | 8/1998 | Flaherty et al. |
| 5,801,637 A | 9/1998 | Lomholt |
| 5,810,734 A | 9/1998 | Caro et al. |
| 5,813,403 A | 9/1998 | Soller et al. |
| 5,822,544 A | 10/1998 | Chaco et al. |
| 5,822,546 A | 10/1998 | George |
| 5,823,950 A | 10/1998 | Diab et al. |
| 5,829,723 A | 11/1998 | Brunner |
| 5,830,131 A | 11/1998 | Caro et al. |
| 5,833,618 A | 11/1998 | Caro et al. |
| 5,855,550 A | 1/1999 | Lai et al. |
| 5,860,919 A | 1/1999 | Kiani-Azarbayjany et al. |
| 5,876,351 A | 3/1999 | Rohde |
| 5,885,214 A | 3/1999 | Monroe et al. |
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,924,074 A | 7/1999 | Evans |
| 5,931,160 A | 8/1999 | Gilmore et al. |
| 5,931,791 A | 8/1999 | Saltzstein et al. |

(56) References Cited

U.S. PATENT DOCUMENTS

| | | |
|---|---|---|
| 5,934,925 A | 8/1999 | Tobler et al. |
| 5,940,182 A | 8/1999 | Lepper, Jr. et al. |
| 5,942,986 A | 8/1999 | Shabot et al. |
| 5,987,343 A | 11/1999 | Kinast |
| 5,987,519 A | 11/1999 | Peifer et al. |
| 5,995,855 A | 11/1999 | Kiani et al. |
| 5,997,343 A | 12/1999 | Mills et al. |
| 6,002,952 A | 12/1999 | Diab et al. |
| 6,006,119 A | 12/1999 | Soller et al. |
| 6,010,937 A | 1/2000 | Karam et al. |
| 6,011,986 A | 1/2000 | Diab et al. |
| 6,014,346 A | 1/2000 | Malone |
| 6,018,673 A | 1/2000 | Chin et al. |
| 6,024,699 A | 2/2000 | Surwit et al. |
| 6,027,452 A | 2/2000 | Flaherty et al. |
| 6,032,678 A | 3/2000 | Rottem |
| 6,035,230 A | 3/2000 | Kang |
| 6,036,642 A | 3/2000 | Diab et al. |
| 6,036,718 A | 3/2000 | Ledford et al. |
| 6,040,578 A | 3/2000 | Malin et al. |
| 6,045,509 A | 4/2000 | Caro et al. |
| 6,045,527 A | 4/2000 | Appelbaum et al. |
| 6,057,758 A | 5/2000 | Dempsey et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,093,146 A | 7/2000 | Filangeri |
| 6,101,478 A | 8/2000 | Brown |
| 6,106,463 A | 8/2000 | Wilk |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,132,218 A | 10/2000 | Benja-Athon |
| 6,139,494 A | 10/2000 | Cairnes |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A | 12/2000 | Schmidt et al. |
| D437,058 S | 1/2001 | Gozani |
| 6,168,563 B1 | 1/2001 | Brown |
| 6,171,237 B1 | 1/2001 | Avitall et al. |
| 6,175,752 B1 | 1/2001 | Say et al. |
| 6,183,417 B1 | 2/2001 | Geheb et al. |
| 6,184,521 B1 | 2/2001 | Coffin, IV et al. |
| 6,185,448 B1 | 2/2001 | Borovsky |
| 6,195,576 B1 | 2/2001 | John |
| 6,206,830 B1 | 3/2001 | Diab et al. |
| 6,221,012 B1 | 4/2001 | Maschke et al. |
| 6,224,553 B1 | 5/2001 | Nevo |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,241,684 B1 | 6/2001 | Amano et al. |
| 6,251,113 B1 | 6/2001 | Appelbaum |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,304,767 B1 | 10/2001 | Soller et al. |
| 6,308,089 B1 | 10/2001 | von der Ruhr et al. |
| 6,312,378 B1 | 11/2001 | Bardy |
| 6,317,627 B1 | 11/2001 | Ennen et al. |
| 6,321,100 B1 | 11/2001 | Parker |
| 6,322,502 B1 | 11/2001 | Schoenberg et al. |
| 6,325,761 B1 | 12/2001 | Jay |
| 6,329,139 B1 | 12/2001 | Nova et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,352,504 B1 | 3/2002 | Ise |
| 6,354,235 B1 | 3/2002 | Davies |
| 6,360,114 B1 | 3/2002 | Diab et al. |
| 6,364,834 B1 | 4/2002 | Reuss et al. |
| 6,364,839 B1 | 4/2002 | Little et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,476 B1 | 5/2002 | Osadchy et al. |
| 6,385,589 B1 | 5/2002 | Trusheim et al. |
| 6,388,240 B2 | 5/2002 | Schulz et al. |
| 6,397,091 B2 | 5/2002 | Diab et al. |
| 6,407,335 B1 | 6/2002 | Franklin-Lees |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,470,893 B1 | 12/2002 | Boesen |
| 6,501,975 B2 | 12/2002 | Diab et al. |
| 6,505,059 B1 | 1/2003 | Kollias et al. |
| 6,515,273 B2 | 2/2003 | Al-Ali |
| 6,516,289 B2 | 2/2003 | David et al. |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,551,243 B2 | 4/2003 | Bocionek et al. |
| 6,570,592 B1 | 5/2003 | Sajdak et al. |
| 6,578,428 B1 | 6/2003 | Dromms et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,616,606 B1 | 9/2003 | Peterson et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,641,533 B2 | 11/2003 | Causey et al. |
| 6,643,530 B2 | 11/2003 | Diab et al. |
| 6,646,556 B1 | 11/2003 | Smith et al. |
| 6,650,917 B2 | 11/2003 | Diab et al. |
| 6,650,939 B2 | 11/2003 | Takpke, II et al. |
| 6,654,624 B2 | 11/2003 | Diab et al. |
| D483,872 S | 12/2003 | Cruz et al. |
| 6,658,276 B2 | 12/2003 | Kiani et al. |
| 6,661,161 B1 | 12/2003 | Lanzo et al. |
| 6,663,570 B2 | 12/2003 | Mott et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,694,180 B1 | 2/2004 | Boesen |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |

(56) References Cited

U.S. PATENT DOCUMENTS

| | | |
|---|---|---|
| 6,699,194 B1 | 3/2004 | Diab et al. |
| 6,707,476 B1 * | 3/2004 | Hochstedler ........ G06F 19/3418 715/789 |
| 6,714,804 B2 | 3/2004 | Al-Ali et al. |
| RE38,492 E | 4/2004 | Diab et al. |
| 6,719,694 B2 | 4/2004 | Weng et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,725,086 B2 | 4/2004 | Marinello |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,746,406 B2 | 6/2004 | Lia et al. |
| 6,750,463 B1 | 6/2004 | Riley |
| 6,751,492 B2 | 6/2004 | Ben-haim |
| 6,760,607 B2 | 7/2004 | Al-Ali |
| 6,766,188 B2 | 7/2004 | Soller |
| 6,770,028 B1 | 8/2004 | Ali et al. |
| 6,771,994 B2 | 8/2004 | Kiani et al. |
| 6,773,396 B2 | 8/2004 | Flach et al. |
| 6,783,492 B2 | 8/2004 | Dominguez |
| 6,788,965 B2 | 9/2004 | Ruchti et al. |
| 6,790,178 B1 | 9/2004 | Mault et al. |
| 6,792,300 B1 | 9/2004 | Diab et al. |
| 6,795,724 B2 | 9/2004 | Hogan |
| 6,796,186 B2 | 9/2004 | Lia et al. |
| 6,804,656 B1 | 10/2004 | Rosenfeld |
| 6,807,050 B1 | 10/2004 | Whitehorn et al. |
| 6,813,511 B2 | 11/2004 | Diab et al. |
| 6,816,241 B2 | 11/2004 | Grubisic |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,876,931 B2 | 4/2005 | Lorenz et al. |
| 6,897,788 B2 | 5/2005 | Khair et al. |
| 6,898,452 B2 | 5/2005 | Al-Ali et al. |
| 6,907,237 B1 | 6/2005 | Dorenbosch et al. |
| 6,915,149 B2 | 7/2005 | Ben-haim |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,952,340 B2 | 10/2005 | Son |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,983,179 B2 | 1/2006 | Ben-haim |
| 6,985,764 B2 | 1/2006 | Mason et al. |
| 6,988,989 B2 | 1/2006 | Weiner et al. |
| 6,990,087 B2 | 1/2006 | Rao et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,884 B2 | 2/2006 | Ulmsten |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,044,918 B2 | 5/2006 | Diab |
| 7,044,930 B2 | 5/2006 | Stromberg |
| 7,048,687 B1 | 5/2006 | Reuss et al. |
| 7,059,769 B1 | 6/2006 | Potega |
| 7,063,666 B2 | 6/2006 | Weng et al. |
| 7,067,893 B2 | 6/2006 | Mills et al. |
| 7,079,035 B2 | 7/2006 | Bock et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,229,415 B2 | 6/2007 | Schwartz |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,373 B2 | 7/2007 | Soller et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,256,708 B2 | 8/2007 | Rosenfeld |
| 7,261,697 B2 | 8/2007 | Berstein |
| 7,264,616 B2 | 9/2007 | Shehada et al. |
| 7,267,671 B2 | 9/2007 | Shehada et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,285,090 B2 | 10/2007 | Stivoric |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,307,543 B2 | 12/2007 | Rosenfeld |
| 7,313,423 B2 | 12/2007 | Griffin et al. |
| 7,314,446 B2 | 1/2008 | Byrd et al. |
| 7,315,825 B2 | 1/2008 | Rosenfeld |
| 7,321,862 B2 | 1/2008 | Rosenfeld |
| 7,322,971 B2 | 1/2008 | Shehada et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,178 B2 | 4/2008 | Ziel et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,378,975 B1 | 5/2008 | Smith et al. |
| 7,382,247 B2 | 6/2008 | Welch et al. |

(56) References Cited

U.S. PATENT DOCUMENTS

| | | |
|---|---|---|
| 7,383,070 B2 | 6/2008 | Diab et al. |
| 7,390,299 B2 | 6/2008 | Weiner et al. |
| 7,395,158 B2 | 7/2008 | Monfre et al. |
| 7,395,216 B2 | 7/2008 | Rosenfeld |
| 7,411,509 B2 | 8/2008 | Rosenfeld |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,439,856 B2 | 10/2008 | Weiner et al. |
| 7,440,787 B2 | 10/2008 | Diab |
| 7,454,240 B2 | 11/2008 | Diab et al. |
| 7,454,359 B2 | 11/2008 | Rosenfeld |
| 7,454,360 B2 | 11/2008 | Rosenfeld |
| 7,462,151 B2 | 12/2008 | Childre et al. |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,483,729 B2 | 1/2009 | Al-Ali et al. |
| 7,483,730 B2 | 1/2009 | Diab et al. |
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,515,043 B2 | 4/2009 | Welch et al. |
| 7,515,044 B2 | 4/2009 | Welch et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 | 5/2009 | Soyemi et al. |
| 7,549,961 B1 | 6/2009 | Hwang |
| 7,551,717 B2 | 6/2009 | Tome et al. |
| 7,559,520 B2 | 7/2009 | Quijano et al. |
| 7,563,110 B2 | 7/2009 | Al-Ali et al. |
| 7,577,475 B2 | 8/2009 | Consentino et al. |
| 7,590,950 B2 | 9/2009 | Collins et al. |
| 7,593,230 B2 | 9/2009 | Abul-Haj et al. |
| 7,596,398 B2 | 9/2009 | Al-Ali et al. |
| 7,597,665 B2 | 10/2009 | Wilk et al. |
| 7,606,608 B2 | 10/2009 | Blank et al. |
| 7,612,999 B2 | 11/2009 | Clark et al. |
| 7,616,303 B2 | 11/2009 | Yang et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,639,145 B2 | 12/2009 | Lawson et al. |
| 7,640,140 B2 | 12/2009 | Ruchti et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| 7,654,966 B2 | 2/2010 | Westinskow et al. |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,722,542 B2 | 5/2010 | Lia et al. |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,740,590 B2 | 6/2010 | Bernstein |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,515 S | 8/2010 | Chua et al. |
| D621,516 S | 8/2010 | Kiani et al. |
| 7,766,818 B2 | 8/2010 | Iketani et al. |
| 7,772,799 B2 | 8/2010 | Wu |
| 7,774,060 B2 | 8/2010 | Westenskow et al. |
| 7,778,851 B2 | 8/2010 | Schoenberg et al. |
| 7,791,155 B2 | 9/2010 | Diab |
| 7,794,407 B2 | 9/2010 | Rothenberg |
| 7,801,581 B2 | 9/2010 | Diab |
| 7,806,830 B2 | 10/2010 | Bernstein |
| 7,820,184 B2 | 10/2010 | Strizker et al. |
| 7,822,452 B2 | 10/2010 | Schurman et al. |
| RE41,912 E | 11/2010 | Parker |
| 7,831,450 B2 | 11/2010 | Schoenberg |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,935 B2 | 12/2010 | Gotlib |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,881,892 B2 | 2/2011 | Soyemi et al. |
| 7,884,314 B2 | 2/2011 | Hamada |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Al-Ali et al. |
| 7,991,463 B2 | 8/2011 | Kelleher et al. |
| 7,991,625 B2 | 8/2011 | Rosenfeld |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |

(56) References Cited

U.S. PATENT DOCUMENTS

| | | |
|---|---|---|
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| 8,094,013 B1 | 1/2012 | Lee et al. |
| 8,107,397 B1 | 1/2012 | Bagchi et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| D659,836 S | 5/2012 | Bensch et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,182,429 B2 | 5/2012 | Mason |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,200,308 B2 | 6/2012 | Zhang et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,235,907 B2 | 8/2012 | Wilk et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,294,588 B2 | 10/2012 | Fisher et al. |
| 8,294,716 B2 | 10/2012 | William et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| RE43,860 E | 12/2012 | Parker |
| 8,326,649 B2 | 12/2012 | Rosenfeld |
| 8,328,793 B2 | 12/2012 | Birkenbach et al. |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,360,936 B2 | 1/2013 | Dibenedetto et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| D679,018 S | 3/2013 | Fullerton et al. |
| 8,388,353 B2 | 3/2013 | Kiani et al. |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,167 B2 | 7/2013 | Buxton et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,565,847 B2 | 10/2013 | Buxton et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,578,082 B2 | 11/2013 | Medina et al. |
| 8,579,813 B2 | 11/2013 | Causey |
| 8,581,732 B2 | 11/2013 | Al-Ali et al. |
| 8,588,880 B2 | 11/2013 | Abdul-Hafiz et al. |
| 8,588,924 B2 | 11/2013 | Dion |
| 8,597,287 B2 | 12/2013 | Benamou et al. |
| 8,600,467 B2 | 12/2013 | Al-Ali et al. |
| 8,600,777 B2 | 12/2013 | Schoenberg |
| 8,606,342 B2 | 12/2013 | Diab |
| 8,620,678 B2 | 12/2013 | Gotlib |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,771 B2 | 4/2014 | Wekell et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |

(56) References Cited

U.S. PATENT DOCUMENTS

| | | |
|---|---|---|
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,753,274 B2 | 6/2014 | Ziv et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,758,020 B2 | 6/2014 | Burdea et al. |
| 8,761,850 B2 | 6/2014 | Lamego |
| D709,846 S | 7/2014 | Oswaks |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,950 B2 | 7/2014 | Larsen et al. |
| 8,801,613 B2 | 8/2014 | Al-Ali et al. |
| 8,818,477 B2 | 8/2014 | Soller |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,866,620 B2 | 10/2014 | Amir |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,873,035 B2 | 10/2014 | Yang et al. |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,907,287 B2 | 12/2014 | Vanderpohl |
| 8,909,310 B2 | 12/2014 | Lamego et al. |
| 8,909,330 B2 | 12/2014 | McCombie et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,951,248 B2 | 2/2015 | Messerly et al. |
| 8,956,292 B2 | 2/2015 | Wekell et al. |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,057,689 B2 | 6/2015 | Soller |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,291 B2 | 8/2015 | Soller |
| 9,095,316 B2 | 8/2015 | Welch et al. |
| 9,104,789 B2 | 8/2015 | Gross et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,125,578 B2 | 9/2015 | Grunwald |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,262,586 B2 | 2/2016 | Steiger et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,414,784 B1 | 8/2016 | Berme et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,529,762 B2 | 12/2016 | Gisler et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |

(56) References Cited

U.S. PATENT DOCUMENTS

| | | |
|---|---|---|
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Al-Ali et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | Dejong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |

(56) References Cited

U.S. PATENT DOCUMENTS

| | | |
|---|---|---|
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,512,436 B2 | 12/2019 | Muhsin et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| 10,667,764 B2 | 6/2020 | Ahmed et al. |
| 2001/0011355 A1 | 8/2001 | Kawai |
| 2001/0031922 A1 | 10/2001 | Weng et al. |
| 2001/0034477 A1 | 10/2001 | Mansfield et al. |
| 2001/0039199 A1 | 11/2001 | Shinzaki |
| 2001/0039483 A1 | 11/2001 | Brand et al. |
| 2001/0046366 A1 | 11/2001 | Susskind |
| 2001/0046862 A1 | 11/2001 | Coppinger et al. |
| 2001/0055978 A1 | 12/2001 | Herrod et al. |
| 2002/0010401 A1 | 1/2002 | Bushmakin et al. |
| 2002/0032386 A1 | 3/2002 | Sackner et al. |
| 2002/0038392 A1 | 3/2002 | De La Huerga |
| 2002/0045836 A1 | 4/2002 | Alkawwas |
| 2002/0052311 A1 | 5/2002 | Solomon et al. |
| 2002/0058864 A1 | 5/2002 | Mansfield et al. |
| 2002/0063690 A1 | 5/2002 | Chung et al. |
| 2002/0133080 A1 | 9/2002 | Apruzzese et al. |
| 2002/0140675 A1 | 10/2002 | Ali et al. |
| 2002/0165462 A1 | 11/2002 | Westbrook et al. |
| 2002/0177758 A1 | 11/2002 | Schoenberg |
| 2002/0198445 A1 | 12/2002 | Dominguez et al. |
| 2003/0013975 A1 | 1/2003 | Kiani |
| 2003/0018243 A1 | 1/2003 | Gerhardt et al. |
| 2003/0027326 A1 | 2/2003 | Ulmsten et al. |
| 2003/0052787 A1 | 3/2003 | Zerhusen et al. |
| 2003/0058838 A1 | 3/2003 | Wengrovitz |
| 2003/0144582 A1 | 7/2003 | Cohen et al. |
| 2003/0156288 A1 | 8/2003 | Barnum et al. |
| 2003/0158466 A1 | 8/2003 | Lynn et al. |
| 2003/0212312 A1 | 11/2003 | Coffin, IV et al. |
| 2003/0216670 A1 | 11/2003 | Beggs |
| 2004/0013647 A1 | 1/2004 | Solomon et al. |
| 2004/0073095 A1 | 4/2004 | Causey et al. |
| 2004/0106163 A1 | 6/2004 | Workman, Jr. et al. |
| 2004/0122787 A1 | 6/2004 | Avinash et al. |
| 2004/0126007 A1 | 7/2004 | Ziel et al. |
| 2004/0139571 A1 | 7/2004 | Chang et al. |
| 2004/0147818 A1 | 7/2004 | Levy et al. |
| 2004/0152957 A1 | 8/2004 | Stivoric et al. |
| 2004/0179332 A1 | 9/2004 | Smith et al. |
| 2004/0186357 A1 | 9/2004 | Soderberg et al. |
| 2004/0230118 A1 | 11/2004 | Shehada et al. |
| 2004/0230132 A1 | 11/2004 | Shehada et al. |
| 2004/0230179 A1 | 11/2004 | Shehada et al. |
| 2004/0243017 A1 | 12/2004 | Causevic |
| 2004/0249670 A1 | 12/2004 | Noguchi et al. |
| 2004/0254431 A1 | 12/2004 | Shehada et al. |
| 2004/0254432 A1 | 12/2004 | Shehada et al. |
| 2004/0267103 A1 | 12/2004 | Li et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0055276 A1 | 3/2005 | Kiani et al. |
| 2005/0065417 A1 | 3/2005 | Ali et al. |
| 2005/0080336 A1 | 4/2005 | Byrd et al. |
| 2005/0096542 A1 | 5/2005 | Weng et al. |
| 2005/0101849 A1* | 5/2005 | Al-Ali ............... A61B 5/0002 600/323 |
| 2005/0113653 A1 | 5/2005 | Fox et al. |
| 2005/0124864 A1 | 6/2005 | Mack et al. |
| 2005/0125256 A1 | 6/2005 | Schoenberg |
| 2005/0164933 A1 | 7/2005 | Tymianski et al. |
| 2005/0171444 A1 | 8/2005 | Ono et al. |
| 2005/0188083 A1 | 8/2005 | Biondi et al. |
| 2005/0191294 A1 | 9/2005 | Arap et al. |
| 2005/0234317 A1 | 10/2005 | Kiani |
| 2005/0268401 A1 | 12/2005 | Dixon et al. |
| 2005/0277872 A1 | 12/2005 | Colby et al. |
| 2006/0049936 A1 | 3/2006 | Collins, Jr. et al. |
| 2006/0052718 A1 | 3/2006 | Parnagian |
| 2006/0058647 A1 | 3/2006 | Strommer et al. |
| 2006/0073719 A1 | 4/2006 | Kiani |
| 2006/0089543 A1 | 4/2006 | Kim et al. |
| 2006/0094936 A1 | 5/2006 | Russ |
| 2006/0149393 A1 | 7/2006 | Calderon |
| 2006/0155175 A1 | 7/2006 | Ogino et al. |
| 2006/0161054 A1 | 7/2006 | Reuss et al. |
| 2006/0189871 A1 | 8/2006 | Al-Ali et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2007/0000490 A1 | 1/2007 | DeVries et al. |
| 2007/0002533 A1 | 1/2007 | Kogan et al. |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0073116 A1 | 3/2007 | Kiani et al. |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118399 A1 | 5/2007 | Avinash et al. |
| 2007/0140475 A1 | 6/2007 | Kurtock et al. |
| 2007/0156033 A1 | 7/2007 | Causey et al. |
| 2007/0157285 A1 | 7/2007 | Frank et al. |
| 2007/0159332 A1 | 7/2007 | Koblasz |
| 2007/0163589 A1 | 7/2007 | DeVries et al. |
| 2007/0180140 A1 | 8/2007 | Welch et al. |
| 2007/0185390 A1 | 8/2007 | Perkins et al. |
| 2007/0232941 A1 | 10/2007 | Rabinovich |
| 2007/0244377 A1 | 10/2007 | Cozad et al. |
| 2007/0244724 A1 | 10/2007 | Pendergast et al. |
| 2007/0254593 A1 | 11/2007 | Jollota et al. |
| 2007/0255114 A1 | 11/2007 | Ackermann et al. |
| 2007/0255116 A1 | 11/2007 | Mehta et al. |
| 2007/0255250 A1 | 11/2007 | Moberg |
| 2007/0282478 A1 | 12/2007 | Al-Ali et al. |
| 2007/0293906 A1 | 12/2007 | Cowan et al. |
| 2008/0000479 A1 | 1/2008 | Elaz et al. |
| 2008/0003200 A1 | 1/2008 | Arap et al. |

(56) References Cited

U.S. PATENT DOCUMENTS

| | | |
|---|---|---|
| 2008/0021854 A1 | 1/2008 | Jung et al. |
| 2008/0033661 A1 | 2/2008 | Syroid et al. |
| 2008/0039701 A1 | 2/2008 | Ali et al. |
| 2008/0053438 A1 | 3/2008 | DeVries et al. |
| 2008/0058657 A1 | 3/2008 | Schwartz et al. |
| 2008/0064965 A1 | 3/2008 | Jay et al. |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0094228 A1 | 4/2008 | Welch et al. |
| 2008/0097167 A1 | 4/2008 | Yudkovitch et al. |
| 2008/0099366 A1 | 5/2008 | Niemiec et al. |
| 2008/0108884 A1 | 5/2008 | Kiani |
| 2008/0119412 A1 | 5/2008 | Tymianski et al. |
| 2008/0138278 A1 | 6/2008 | Scherz et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0194918 A1 | 8/2008 | Kulik et al. |
| 2008/0208912 A1 | 8/2008 | Garibaldi |
| 2008/0215627 A1 | 9/2008 | Higgins et al. |
| 2008/0221396 A1 | 9/2008 | Garces et al. |
| 2008/0221418 A1 | 9/2008 | Al-Ali et al. |
| 2008/0228077 A1 | 9/2008 | Wilk et al. |
| 2008/0275309 A1 | 11/2008 | Stivoric et al. |
| 2008/0281167 A1 | 11/2008 | Soderberg et al. |
| 2008/0281168 A1* | 11/2008 | Gibson ............... A61B 5/0205 600/301 |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0139354 A1 | 12/2008 | Bell et al. |
| 2008/0300020 A1 | 12/2008 | Nishizawa et al. |
| 2008/0319275 A1 | 12/2008 | Chiu et al. |
| 2008/0319354 A1 | 12/2008 | Bell et al. |
| 2009/0005651 A1 | 1/2009 | Ward et al. |
| 2009/0018808 A1 | 1/2009 | Bronstein et al. |
| 2009/0024008 A1 | 1/2009 | Brunner et al. |
| 2009/0036759 A1 | 2/2009 | Ault et al. |
| 2009/0043172 A1 | 2/2009 | Zagorchev et al. |
| 2009/0052623 A1 | 2/2009 | Tome et al. |
| 2009/0054735 A1 | 2/2009 | Higgins et al. |
| 2009/0054743 A1 | 2/2009 | Stewart |
| 2009/0062682 A1 | 3/2009 | Bland et al. |
| 2009/0069642 A1 | 3/2009 | Gao et al. |
| 2009/0093687 A1 | 4/2009 | Telfort et al. |
| 2009/0095926 A1 | 4/2009 | MacNeish, III |
| 2009/0099480 A1 | 4/2009 | Salgo et al. |
| 2009/0119330 A1 | 5/2009 | Sampath et al. |
| 2009/0119843 A1 | 5/2009 | Rodgers et al. |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171170 A1 | 7/2009 | Li et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0221887 A1 | 9/2009 | Mannheimer et al. |
| 2009/0226372 A1 | 9/2009 | Ruoslahti et al. |
| 2009/0247984 A1 | 10/2009 | Lamego et al. |
| 2009/0264778 A1 | 10/2009 | Markowitz et al. |
| 2009/0275813 A1 | 11/2009 | Davis |
| 2009/0275844 A1 | 11/2009 | Al-Ali |
| 2009/0281462 A1 | 11/2009 | Heliot et al. |
| 2009/0299157 A1 | 12/2009 | Telfort et al. |
| 2009/0309755 A1 | 12/2009 | Williamson et al. |
| 2009/0322540 A1 | 12/2009 | Richardson et al. |
| 2009/0326386 A1 | 12/2009 | Sethi et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0060747 A1 | 3/2010 | Woodman |
| 2010/0069725 A1 | 3/2010 | Al-Ali |
| 2010/0081895 A1 | 4/2010 | Zand |
| 2010/0099964 A1 | 4/2010 | O'Reilly et al. |
| 2010/0114254 A1 | 5/2010 | Kornet |
| 2010/0125217 A1 | 5/2010 | Kuo et al. |
| 2010/0144627 A1 | 6/2010 | Vitek et al. |
| 2010/0145146 A1 | 6/2010 | Melder |
| 2010/0177100 A1 | 7/2010 | Carnes et al. |
| 2010/0185101 A1 | 7/2010 | Sakai et al. |
| 2010/0198622 A1 | 8/2010 | Gajic et al. |
| 2010/0210958 A1 | 8/2010 | Manwaring et al. |
| 2010/0234706 A1 | 9/2010 | Gilland |
| 2010/0234718 A1 | 9/2010 | Sampath et al. |
| 2010/0240945 A1 | 9/2010 | Bikko |
| 2010/0241115 A1 | 9/2010 | Benamou et al. |
| 2010/0249540 A1 | 9/2010 | Lisogurski |
| 2010/0261979 A1 | 10/2010 | Kiani |
| 2010/0270257 A1 | 10/2010 | Wachman et al. |
| 2010/0298657 A1 | 11/2010 | McCombie et al. |
| 2010/0298659 A1 | 11/2010 | Mccombie et al. |
| 2010/0298661 A1 | 11/2010 | Mccombie et al. |
| 2010/0298742 A1 | 11/2010 | Perlman et al. |
| 2010/0305412 A1 | 12/2010 | Darrah et al. |
| 2010/0312103 A1 | 12/2010 | Gorek et al. |
| 2010/0317936 A1 | 12/2010 | Al-Ali et al. |
| 2010/0317951 A1 | 12/2010 | Rutkowski et al. |
| 2011/0001605 A1 | 1/2011 | Kiani et al. |
| 2011/0015533 A1 | 1/2011 | Cox et al. |
| 2011/0021930 A1 | 1/2011 | Mazzeo et al. |
| 2011/0023130 A1 | 1/2011 | Gudgel et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0046495 A1 | 2/2011 | Osypka |
| 2011/0066051 A1 | 3/2011 | Moon et al. |
| 2011/0077473 A1 | 3/2011 | Lisogurski |
| 2011/0077487 A1 | 3/2011 | Buxton et al. |
| 2011/0077488 A1 | 3/2011 | Buxton et al. |
| 2011/0078596 A1 | 3/2011 | Rawlins et al. |
| 2011/0080294 A1 | 4/2011 | Tanishima et al. |
| 2011/0082711 A1 | 4/2011 | Poeze et al. |
| 2011/0087081 A1 | 4/2011 | Kiani et al. |
| 2011/0087083 A1 | 4/2011 | Poeze et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0098583 A1 | 4/2011 | Pandia et al. |
| 2011/0105854 A1 | 5/2011 | Kiani et al. |
| 2011/0105956 A1 | 5/2011 | Hirth |
| 2011/0118561 A1 | 5/2011 | Tari et al. |
| 2011/0118573 A1 | 5/2011 | Mckenna |
| 2011/0118616 A1 | 5/2011 | Vajdic et al. |
| 2011/0125060 A1 | 5/2011 | Telfort et al. |
| 2011/0137297 A1 | 6/2011 | Kiani et al. |
| 2011/0152629 A1 | 6/2011 | Eaton et al. |
| 2011/0172498 A1 | 7/2011 | Olsen et al. |
| 2011/0172967 A1 | 7/2011 | Al-Ali et al. |
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208018 A1 | 8/2011 | Kiani |
| 2011/0208073 A1 | 8/2011 | Matsukawa et al. |
| 2011/0209915 A1 | 9/2011 | Telfort et al. |
| 2011/0212090 A1 | 9/2011 | Pedersen et al. |
| 2011/0213212 A1 | 9/2011 | Al-Ali |
| 2011/0227739 A1 | 9/2011 | Gilham et al. |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0257544 A1 | 10/2011 | Kaasinen et al. |
| 2011/0263950 A1 | 10/2011 | Larson et al. |
| 2011/0288383 A1 | 11/2011 | Diab |
| 2011/0295094 A1 | 12/2011 | Doyle et al. |
| 2011/0301444 A1 | 12/2011 | Al-Ali |
| 2011/0307274 A1 | 12/2011 | Thompson et al. |
| 2012/0004579 A1 | 1/2012 | Luo et al. |
| 2012/0029300 A1 | 2/2012 | Paquet |
| 2012/0029304 A1 | 2/2012 | Medina et al. |
| 2012/0029879 A1 | 2/2012 | Sing et al. |

(56) References Cited

U.S. PATENT DOCUMENTS

| | | |
|---|---|---|
| 2012/0041316 A1 | 2/2012 | Al-Ali et al. |
| 2012/0046557 A1 | 2/2012 | Kiani |
| 2012/0059230 A1 | 3/2012 | Teller et al. |
| 2012/0059267 A1 | 3/2012 | Lamego et al. |
| 2012/0071771 A1 | 3/2012 | Behar |
| 2012/0075464 A1 | 3/2012 | Derenne et al. |
| 2012/0088984 A1 | 4/2012 | Al-Ali et al. |
| 2012/0095778 A1 | 4/2012 | Gross et al. |
| 2012/0101353 A1 | 4/2012 | Reggiardo et al. |
| 2012/0116175 A1 | 5/2012 | Al-Ali et al. |
| 2012/0123231 A1 | 5/2012 | O'Reilly |
| 2012/0123799 A1 | 5/2012 | Nolen et al. |
| 2012/0136221 A1 | 5/2012 | Killen et al. |
| 2012/0165629 A1 | 6/2012 | Merritt et al. |
| 2012/0179006 A1 | 7/2012 | Jansen et al. |
| 2012/0184120 A1 | 7/2012 | Basta et al. |
| 2012/0197619 A1 | 8/2012 | Namer Yelin et al. |
| 2012/0203078 A1 | 8/2012 | Sze et al. |
| 2012/0209082 A1 | 8/2012 | Al-Ali |
| 2012/0209084 A1 | 8/2012 | Olsen et al. |
| 2012/0221634 A1 | 8/2012 | Treu et al. |
| 2012/0226117 A1 | 9/2012 | Lamego et al. |
| 2012/0226160 A1 | 9/2012 | Kudoh |
| 2012/0227739 A1 | 9/2012 | Kiani |
| 2012/0239434 A1 | 9/2012 | Breslow et al. |
| 2012/0242501 A1 | 9/2012 | Tran et al. |
| 2012/0265039 A1 | 10/2012 | Kiani |
| 2012/0282583 A1 | 11/2012 | Thaler et al. |
| 2012/0283524 A1 | 11/2012 | Kiani et al. |
| 2012/0284053 A1 | 11/2012 | Rosenfeld |
| 2012/0286955 A1 | 11/2012 | Welch et al. |
| 2012/0294801 A1 | 11/2012 | Scherz et al. |
| 2012/0296178 A1 | 11/2012 | Lamego et al. |
| 2012/0302894 A1 | 11/2012 | Diab et al. |
| 2012/0303476 A1 | 11/2012 | Krzyzanowski et al. |
| 2012/0319816 A1 | 12/2012 | Al-Ali |
| 2012/0330112 A1 | 12/2012 | Lamego et al. |
| 2013/0006131 A1 | 1/2013 | Narayan et al. |
| 2013/0006151 A1 | 1/2013 | Main et al. |
| 2013/0023775 A1 | 1/2013 | Lamego et al. |
| 2013/0035603 A1 | 2/2013 | Jarausch et al. |
| 2013/0045685 A1 | 2/2013 | Kiani |
| 2013/0046197 A1 | 2/2013 | Dlugos et al. |
| 2013/0046204 A1 | 2/2013 | Lamego et al. |
| 2013/0041591 A1 | 3/2013 | Lamego |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0092805 A1 | 4/2013 | Funk et al. |
| 2013/0096405 A1 | 4/2013 | Garfio |
| 2013/0096936 A1 | 4/2013 | Sampath et al. |
| 2013/0109929 A1 | 5/2013 | Menzel |
| 2013/0109935 A1 | 5/2013 | Al-Ali et al. |
| 2013/0123616 A1 | 5/2013 | Merritt et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0197364 A1 | 8/2013 | Han |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0261494 A1 | 10/2013 | Bloom et al. |
| 2013/0262730 A1 | 10/2013 | Al-Ali et al. |
| 2013/0267793 A1 | 10/2013 | Meador et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0279109 A1 | 10/2013 | Lindblad et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0317393 A1 | 11/2013 | Weiss et al. |
| 2013/0324804 A1 | 12/2013 | McKeown et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0340176 A1 | 12/2013 | Stevens et al. |
| 2013/0345921 A1 | 12/2013 | Al-Ali et al. |
| 2014/0012100 A1 | 1/2014 | Al-Ali et al. |
| 2014/0022081 A1 | 1/2014 | Ribble et al. |
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0046674 A1 | 2/2014 | Rosenfeld |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0073167 A1 | 3/2014 | Al-Ali et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0152673 A1 | 6/2014 | Lynn et al. |
| 2014/0155712 A1 | 6/2014 | Lamego et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0188516 A1 | 7/2014 | Kamen |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266787 A1 | 9/2014 | Tran |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |

(56) References Cited

U.S. PATENT DOCUMENTS

| | | |
|---|---|---|
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0343889 A1 | 11/2014 | Ben Shalom et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0001302 A1 | 1/2015 | Gelay et al. |
| 2015/0005600 A1 | 1/2015 | Blank et al. |
| 2015/0006089 A1 | 1/2015 | Pagels |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0094618 A1 | 4/2015 | Russell et al. |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0246781 A1 | 8/2016 | Cabot |
| 2016/0270717 A1 | 9/2016 | Luna et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224233 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |

(56) References Cited

U.S. PATENT DOCUMENTS

| | | |
|---|---|---|
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0325722 A1 | 10/2019 | Kiani |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |

FOREIGN PATENT DOCUMENTS

| | | |
|---|---|---|
| EP | 2 335 569 A2 | 6/2011 |
| EP | 2766834 | 8/2014 |
| EP | 2811894 | 12/2014 |
| JP | 02-050694 | 2/1990 |
| JP | 09-187428 | 7/1997 |
| JP | 10-336064 | 12/1998 |
| JP | 2000-312668 | 11/2000 |
| JP | 2002-513602 | 5/2002 |
| JP | 2002-165764 | 6/2002 |
| JP | 2002-172096 | 6/2002 |
| JP | 2002-233512 | 8/2002 |
| JP | 2002-535026 | 10/2002 |
| JP | 2002-542493 | 12/2002 |
| JP | 2004-513732 | 5/2004 |
| JP | 2005-038417 | 2/2005 |
| JP | 2008-067931 | 3/2005 |
| JP | 2005-218036 | 8/2005 |
| JP | 2005-295375 | 10/2005 |
| JP | 2007-021213 | 2/2007 |
| JP | 2007-095365 | 4/2007 |
| JP | 2007-174051 | 7/2007 |
| JP | 2008-519635 | 6/2008 |
| JP | 2008-541045 | 11/2008 |
| JP | 2009-017959 | 1/2009 |
| JP | 2009-207836 | 9/2009 |
| JP | 2010-503134 | 1/2010 |
| JP | 2010-093543 | 4/2010 |
| JP | 2010-524510 | 7/2010 |
| JP | 2011-519607 | 7/2011 |
| JP | 2011-519684 | 7/2011 |
| JP | 2011-152261 | 8/2011 |

(56) References Cited

FOREIGN PATENT DOCUMENTS

| JP | 2012-519547 | 8/2012 |
|----|----|----|
| JP | 2014/533997 | 12/2014 |
| JP | 2016-538015 | 12/2016 |
| JP | 2017-047223 | 3/2017 |
| WO | WO 98/29790 | 7/1998 |
| WO | WO 99/13766 | 3/1999 |
| WO | WO 99/056613 | 11/1999 |
| WO | WO 00/063713 | 10/2000 |
| WO | WO 2004/056266 | 7/2004 |
| WO | WO 2004/059551 | 7/2004 |
| WO | WO 2006/051461 | 5/2006 |
| WO | WO 2010/054409 | 5/2010 |
| WO | WO 2011/001302 | 1/2011 |
| WO | WO 2011/002904 | 1/2011 |
| WO | WO 2011/021948 | 2/2011 |
| WO | WO 2011/025549 | 3/2011 |
| WO | WO 2011/041017 | 4/2011 |
| WO | WO 2013/056160 | 4/2013 |
| WO | WO 2013/119982 | 8/2013 |
| WO | WO 2015/054665 | 4/2015 |

OTHER PUBLICATIONS

Extended European Search Report for EP Application No. 10195398.2 dated Jul. 5, 2012.
PCT International Search Report & Written Opinion for Application No. PCT/US2012/060109 in 17 pages.
Wachter, S. Blake; Journal of the American Medical Informatics Association; The Employment of an Iterative Design Process to Develop a Pulmonary Graphical Display. vol. 10, No. 4, Jul./Aug. 2003; pp. 363-372.
Capuano et at. "Remote Telemetry—New Twists for Old Technology." Nursing Management. vol. 26, No. 7. Jul. 1995.
Elmer-Dewitt, Philip, Apple's iWatch: The killer apps may be in hospitals, not health clubs, Fortune.com, Feb. 3, 2014, http://fortune.com/2014/02/03/apples-iwatch-the-killer-apps-may-be-in-hospitals-not-health-clubs/, in 4 pages.
EP Office Action dated Jun. 15, 2015. EP App. No. 10195398.2.
Grundy et al. "Telemedicine in Critical Care: An Experiment in Health Care Delivery." Oct. 1977.
PCT International Preliminary Report on Patentability for Application No. PCT/US2012/060109, dated Apr. 24, 2014.
PCT International Search Report & Written Opinion, App. No. PCT/US2014/060177, dated Dec. 19, 2014.
Grundy et al. "Telemedicine in Critical Care: Problems in design, implementation and assessment." vol. 10, No. 7. Jul. 1982.
PCT International Search Report and Written Opinion, App. No. PCT/US2013/025384, dated Aug. 6, 2013.
Rysavy, "Making the Call with Two-Way Paging", Network Computing, Published Jan. 15, 1997, www.rysavy.com/Articles/twoway.htm.
U.S. Appl. No. 15/448,989, Arm Mountable Portable Patient Monitor, filed Mar. 3, 2017.
U.S. Appl. No. 15/878,172, Arm Mountable Portable Patient Monitor, filed Jan. 23, 2018.
U.S. Appl. No. 15/814,227, Modular Patient Monitor, filed Nov. 15, 2017.
U.S. Appl. No. 13/762,270, Wireless Patient Monitoring Device, filed Feb. 7, 2013.
U.S. Appl. No. 14/834,169, Wireless Patient Monitoring Device, filed Aug. 24, 2015.
U.S. Appl. No. 15/968,392, Medical Monitoring Hub, filed May 1, 2018.
U.S. Appl. No. 15/214,276, Medical Monitoring Hub, filed Jul. 19, 2016.
U.S. Appl. No. 15/919,792, System for Displaying Medical Monitoring Data, filed Mar. 3, 2018.
International Preliminary Report on Patentability & Written Opinion in PCT Application No. PCT/US2013/025384, dated Aug. 21, 2014.
International Preliminary Report on Patentability & Written Opinion in PCT Application No. PCT/US2014/060177, dated Apr. 21, 2016.
U.S. Appl. No. 16/411,689, Physiological Measurement Device, filed May 14, 2019.
U.S. Appl. No. 16/432,240, Modular Patient Monitor, filed Jun. 5, 2019.
U.S. Appl. No. 16/182,427, Wireless Patient Monitoring Device, filed Nov. 6, 2018.
U.S. Appl. No. 16/182,457, Wireless Patient Monitoring Device, filed Nov. 6, 2018.
U.S. Appl. No. 12/840,209, Wireless Patient Monitoring System, filed Jul. 20, 2010.
U.S. Appl. No. 13/010,653, Wireless Patient Monitoring System, filed Jan. 20, 2011.
U.S. Appl. No. 16/670,051, System for Displaying Medical Monitoring Data, filed Oct. 31, 2019.

\* cited by examiner

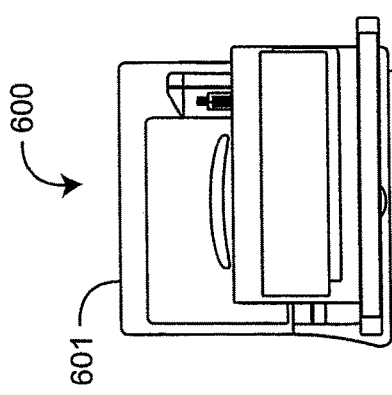
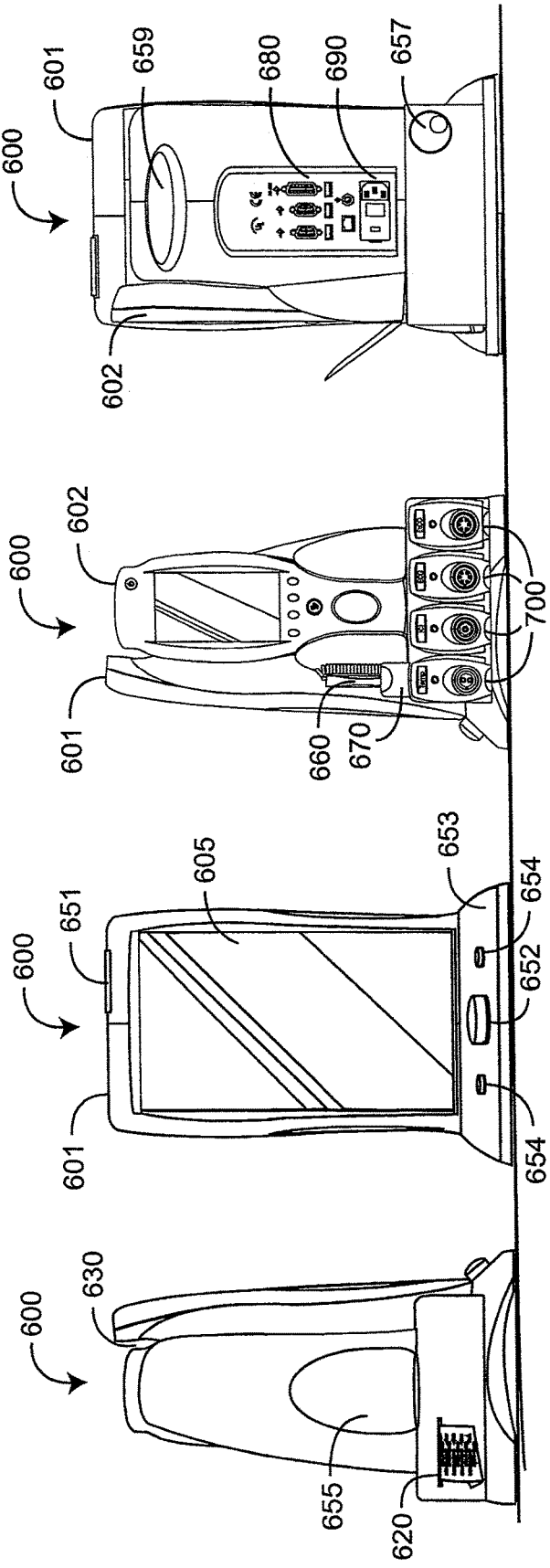
FIG. 6A
FIG. 6B
FIG. 6C
FIG. 6D
FIG. 6E

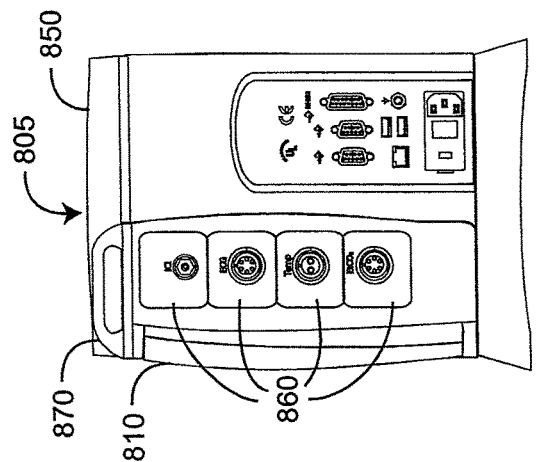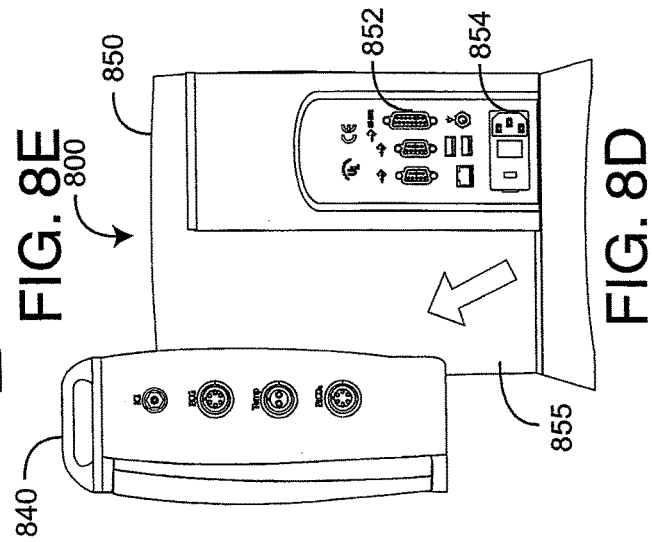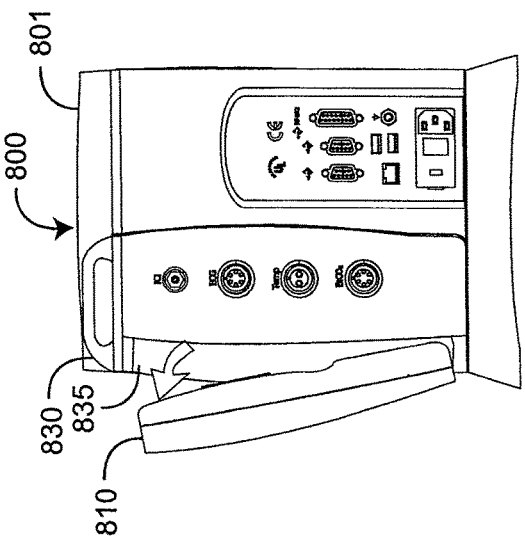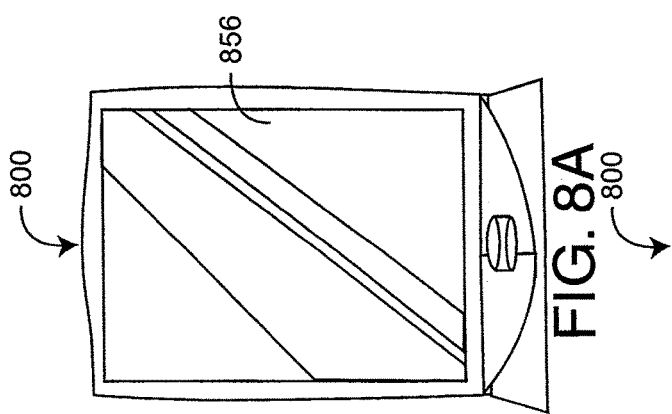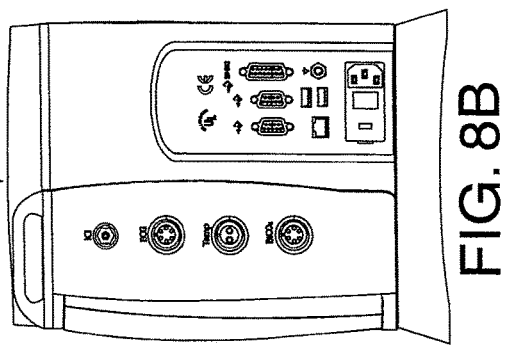
FIG. 8A
FIG. 8B
FIG. 8C
FIG. 8D
FIG. 8E

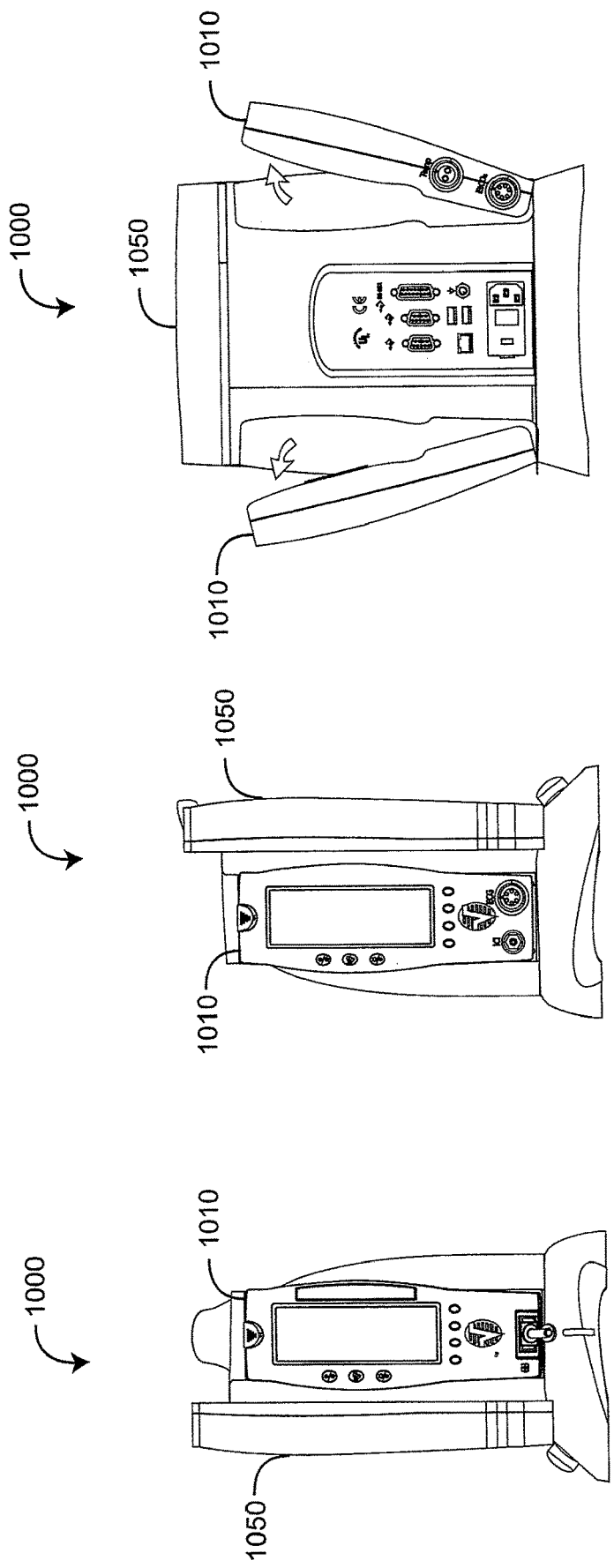

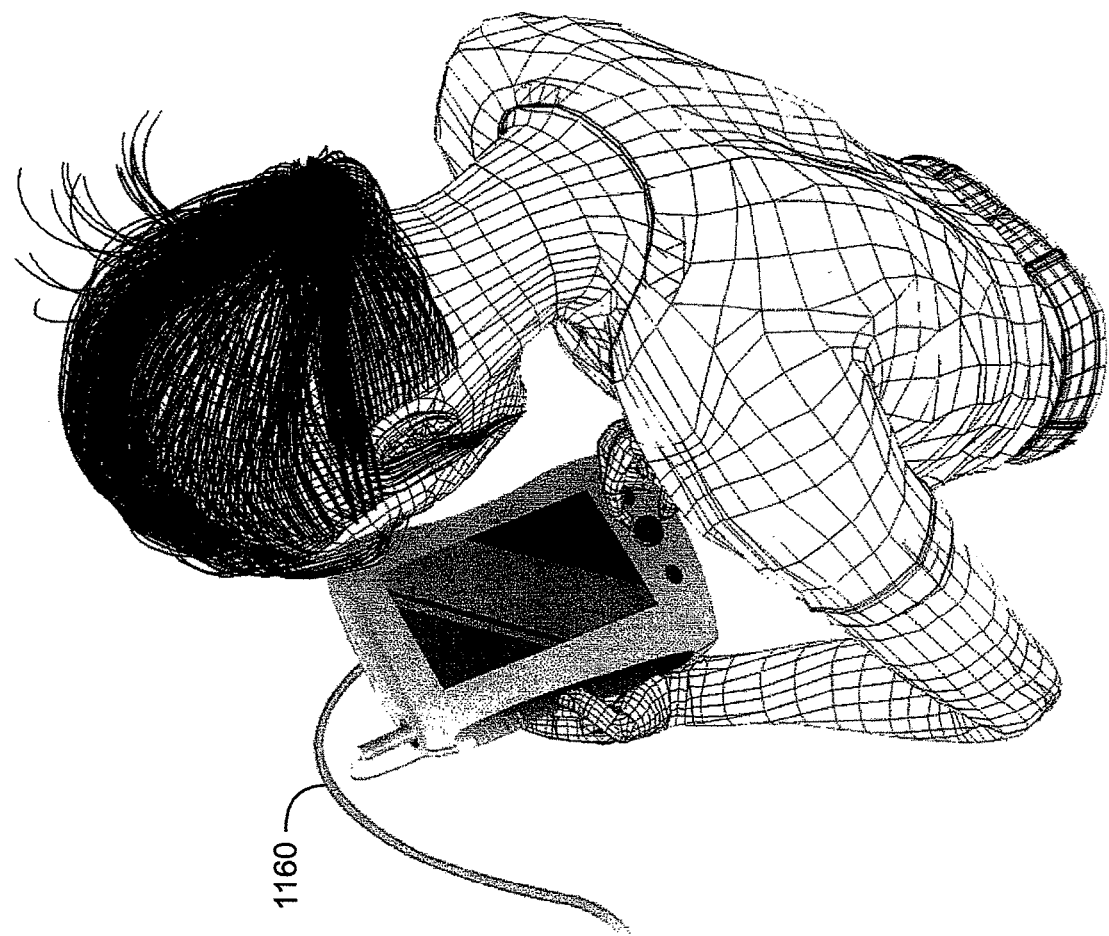
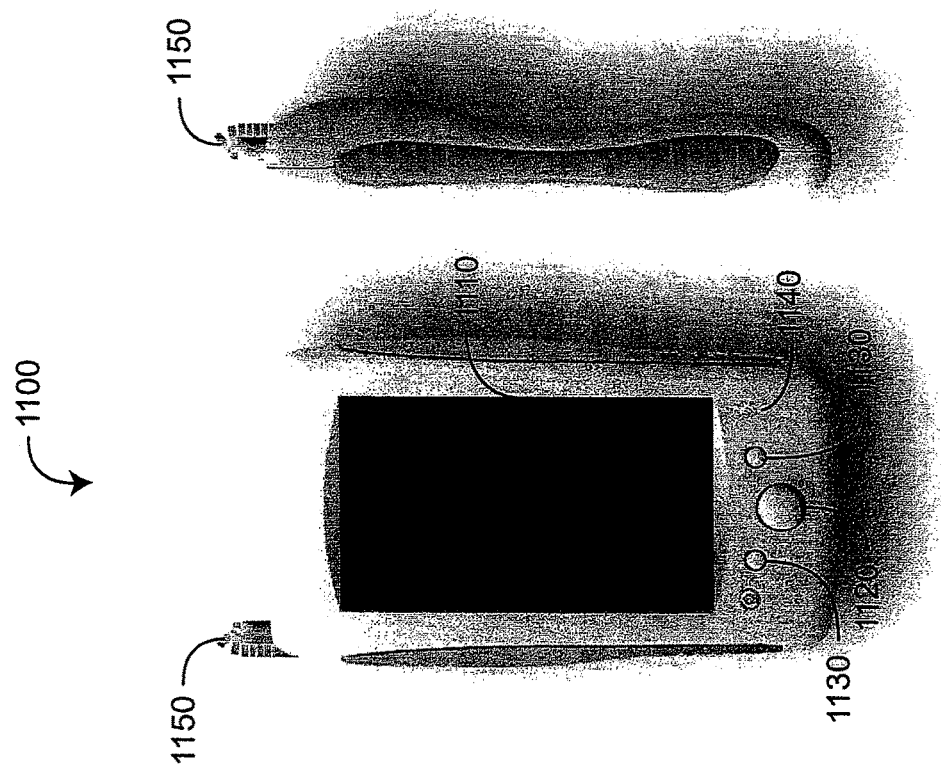
FIG. 11C
FIG. 11B
FIG. 11A

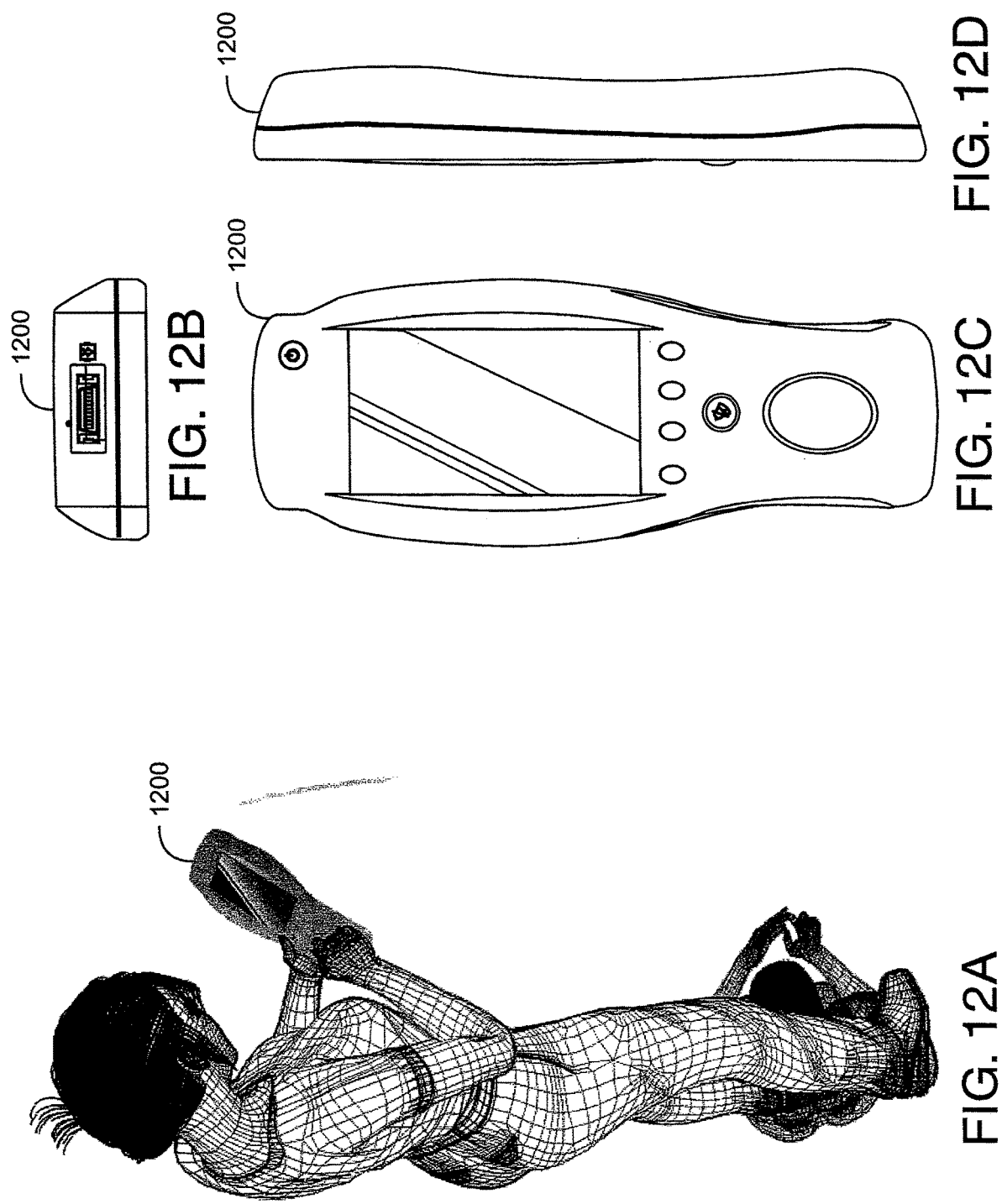

MODULAR PATIENT MONITOR

CROSS-REFERENCE TO RELATED APPLICATIONS

This application is a continuation of U.S. application Ser. No. 11/903,746, filed Sep. 24, 2007, entitled Modular Patient Monitor, which claims the benefit of prior U.S. Provisional Application No. 60/846,471, filed Sep. 22, 2006, entitled Modular Patient Monitor. All of the above-referenced items are hereby incorporated by reference herein in their entireties.

BACKGROUND OF THE INVENTION

Pulse oximetry is a widely accepted continuous and non-invasive method of measuring the level of arterial oxygen saturation in blood. A typical pulse oximetry system has a sensor, a patient monitor and a patient cable. The sensor is placed on a patient fleshy tissue site, usually on the fingertip for adults and the hand or foot for neonates and connected to the patient monitor via the patient cable. The sensor provides a sensor signal detected from the patient tissue site to the patient monitor. The patient monitor displays the calculated data as a percentage value for arterial oxygen saturation (SpO2), as a pulse rate (PR) and as a pulse waveform (plethysmograph or "pleth").

SUMMARY OF THE INVENTION

A modular patient monitor provides a multipurpose, scalable solution for various patient monitoring applications. In an embodiment, a modular patient monitor utilizes multiple wavelength optical sensor and acoustic sensor technologies to provide blood constituent monitoring and acoustic respiration monitoring (ARM) at its core, including pulse oximetry parameters and additional blood parameter measurements such as carboxyhemoglobin (HbCO) and methemoglobin (HbMet). Pulse oximetry monitors and sensors are described in U.S. Pat. No. 5,782,757 entitled Low Noise Optical Probes and U.S. Pat. No. 5,632,272 entitled Signal Processing Apparatus, both incorporated by reference herein. Advanced blood parameter monitors and sensors providing blood parameter measurements in addition to pulse oximetry are described in U.S. patent application Ser. No. 11/367,013, filed Mar. 1, 2006 entitled Multiple Wavelength Sensor Emitters and U.S. patent application Ser. No. 11/367,014, filed Mar. 1, 2006 entitled Non-Invasive Multi-Parameter Monitor, both incorporated by reference herein. Acoustic respiration sensors and monitors are described in U.S. Pat. No. 6,661,161 entitled Piezoelectric Biological Sound Monitor with Printed Circuit Board and U.S. patent application Ser. No. 11/547,570 filed Oct. 6, 2006 entitled Non-Invasive Monitoring of Respiration Rate, Heart Rate and Apnea, both incorporated by reference herein.

Expansion modules provide blood pressure BP, blood glucose, ECG, CO2, depth of sedation and cerebral oximetry to name a few. The modular patient monitor is advantageously scalable in features and cost from a base unit to a high-end unit with the ability to measure multiple parameters from a variety of sensors. In an embodiment, the modular patient monitor incorporates advanced communication features that allow interfacing with other patient monitors and medical devices.

The modular patient monitor is adapted for use in hospital, sub-acute and general floor standalone, multi-parameter measurement applications by physicians, respiratory therapists, registered nurses and other trained clinical caregivers. It can be used in the hospital to interface with central monitoring and remote alarm systems. It also can be used to obtain routine vital signs and advanced diagnostic clinical information and as an in-house transport system with flexibility and portability for patient ambulation. Further uses for the modular patient monitor are clinical research and other data collection.

BRIEF DESCRIPTION OF THE DRAWINGS

FIGS. 6A-E are top, side, front, right and back views of another modular patient monitor embodiment having alternative cartridge embodiments;

FIGS. 8A-E are a front and various back views of yet another modular patient monitor embodiment having a shuttle, including a display and control; a docked shuttle; a docked shuttle with an undocked handheld; an undocked shuttle; and a shuttle having a handheld;

FIGS. 10A-C are side views and a back view, respectively, of an additional modular patient monitor embodiment having dual dockable handhelds;

FIGS. 11A-C are illustrations of a tablet-configured handheld monitor;

FIGS. 12A-D are front perspective, top, front and side views of an alternative handheld embodiment;

DETAILED DESCRIPTION OF THE PREFERRED EMBODIMENTS

Figure 1A:
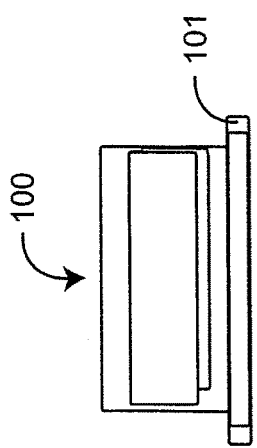
FIGS. 1A-E are top, side, front, right and back views of a modular patient monitor.
Figure 1E:
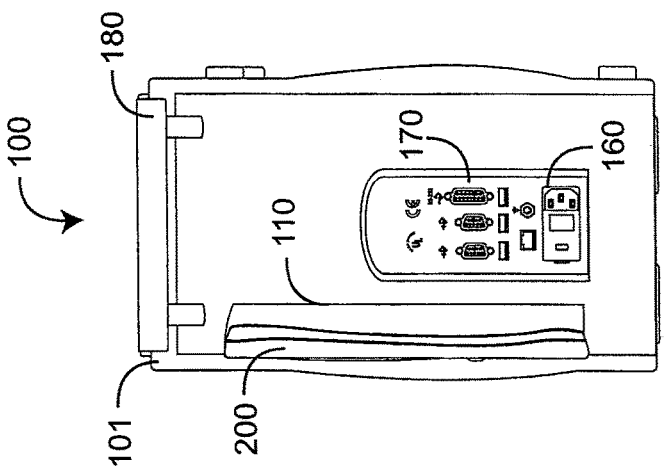
Figure 1C:
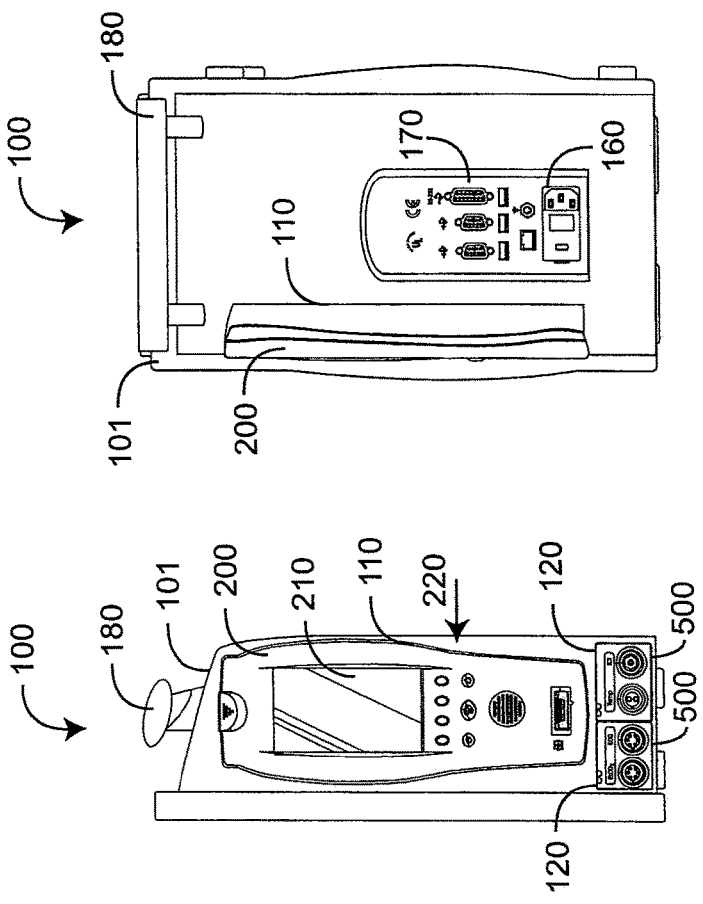

FIGS. 1A-E illustrate a modular patient monitor embodiment 100 having a two-piece modular configuration, a handheld 200 unit and a configurable docking station 101. The handheld 200 docks into a handheld port 110 of the docking station 101, providing the modular patient monitor 100 with two-in-one functionality. In particular, the handheld 200 provides a specific set of clinically relevant parameters. The docking station 101 supports various parameters that are configured to specific hospital environments and/or patient populations including general floor, OR, ICU, ER, NICU, to name a few. Further, the docking station 101 has module ports 120 that accept plug-in expansion modules 500 for additional parameters and technologies. The handheld 200 docked into the docking station 101 allows access to all available parameters providing maximum connectivity, functionality and a larger color display 300. The modular patient monitor 100 provides standalone multi-parameter applications, and the handheld 200 is detachable to provide portability for patient ambulation and in-house transport.

As shown in FIGS. 1A-E, the docking station 101 has a dashboard 130, with a trim knob 140 and buttons 150 so as to support system navigation and data entry. The trim knob 140 is a primary means for system navigation and data entry with an option of a keyboard and mouse as a secondary means.

Figure 1D:
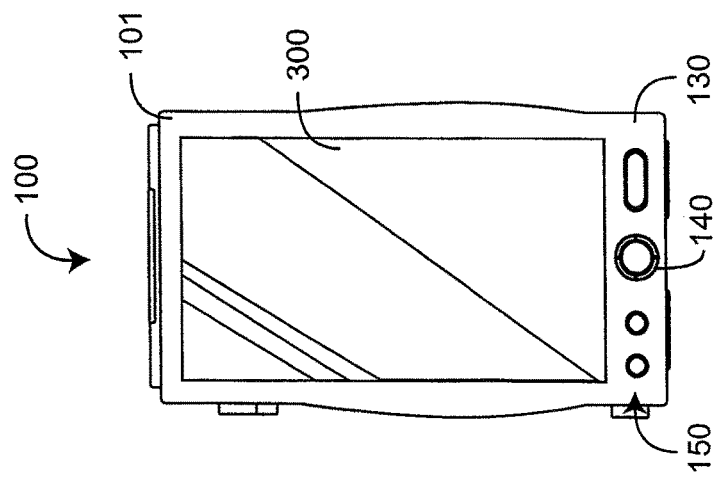
Figure 1B:
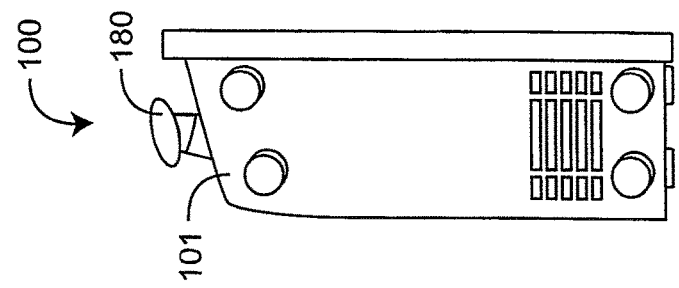

The docking station 101 also has a power supply module 160 and connectivity ports 170. The handheld 200 mechanically attaches to and electrically connects to the docking station 101 when docked, such that the two devices function as one unit and both the handheld display 210 and the docking station display 300 provide user information. In an embodiment, the handheld 200 docks on a docking station side such that the handheld display 200 is visible from that side of the docking station 101 (FIG. 1D). In addition, the docking station 101 has one or more module slots 120 that accommodate external modules 400, as described with respect to FIGS. 4A-C, below.

Also shown in FIGS. 1A-E, controls of the docking station 101 take precedence over those of the handheld 200 when docked. However, the handheld buttons 220 also work for back up purposes. In an embodiment, buttons 150, 220 on the docking station dashboard 130 and on the handheld 200 provide for alarm suspend/silence and mode/enter. The trim knob 140 is the primary method to toggle thru screen menus on the dashboard 130. The procedure includes next, up, down or across page navigation, parameter selection and entry, data entry, alarm limit selection and selection of probe-off detection sensitivity. As a secondary control method, the modular patient monitor 100 has a port for an external keyboard for patient context entry and to navigate the menu. In an embodiment, the docking station 150 has a touch screen. In an embodiment, the modular patient monitor 100 has a bar code scanner module adapted to automatically enter patient context data.

The modular patient monitor 100 includes an integral handle for ease of carrying and dead space for storage for items such as sensors, reusable cables, ICI cable and cuff, EtCO2 hardware and tubing, temperature disposables, acoustic respiratory sensors, power cords and other accessories such as ECG leads, BP cuffs, temperature probes and respiration tapes to name a few. The monitor 100 can operate on AC power or battery power. The modular patient monitor 100 stands upright on a flat surface and allows for flexible mounting such as to an anesthesia machine, bedside table and computer on wheels.

Figure 2B:
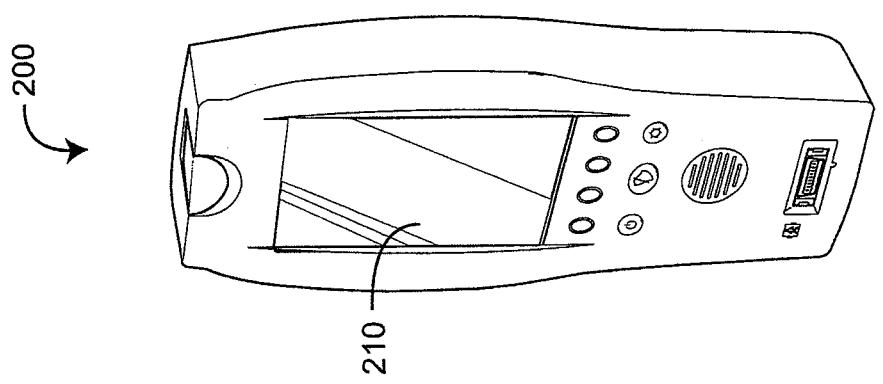
FIGS. 2A-B are front and perspective views of a handheld monitor.
Figure 2A:
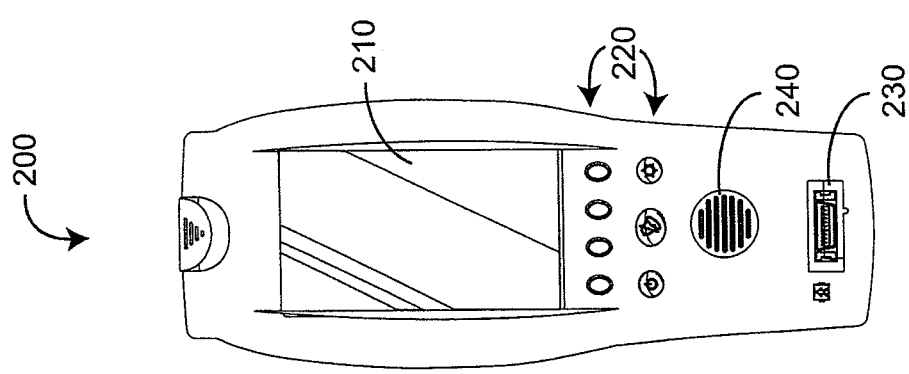

FIGS. 2A-B illustrate a handheld monitor 200, which provides pulse oximetry parameters including oxygen saturation (SpO2), pulse rate (PR), perfusion index (PI), signal quality (SiQ) and a pulse waveform (pleth), among others. In an embodiment, the handheld 200 also provides measurements of other blood constituent parameters that can be derived from a multiple wavelength optical sensor, such as carboxyhemoglobin (HbCO) and methemoglobin (HbMet). The handheld 200 has a color display 210, user interface buttons 220, an optical sensor port 230 and speaker 240. The handheld 200 also has external I/O such as a bar code reader and bedside printer connectivity. The handheld 200 also has a flexible architecture, power and memory headroom to display additional parameters, such as SpvO2, blood glucose, lactate to name a few, derived from other noninvasive sensors such as acoustic, fetal oximetry, blood pressure and ECG sensors to name a few. In an embodiment, the handheld unit 200 has an active matrix (TFT) color display 210, an optional wireless module, an optional interactive touchscreen with on-screen keyboard and a high quality audio system. In another embodiment, the handheld 200 is a Radical or Radical-7™ available from Masimo Corporation, Irvine Calif., which provides Masimo SET® and Masimo Rainbow™ parameters. A color LCD screen handheld user interface is described in U.S. Provisional Patent Application No. 60/846,472 titled Patient Monitor User Interface, filed Sep. 22, 2006 and U.S. patent application Ser. No. 11/904, 046 titled Patient Monitor User Interface, filed Sep. 24, 2007, both applications incorporated by reference herein.

Figure 3:
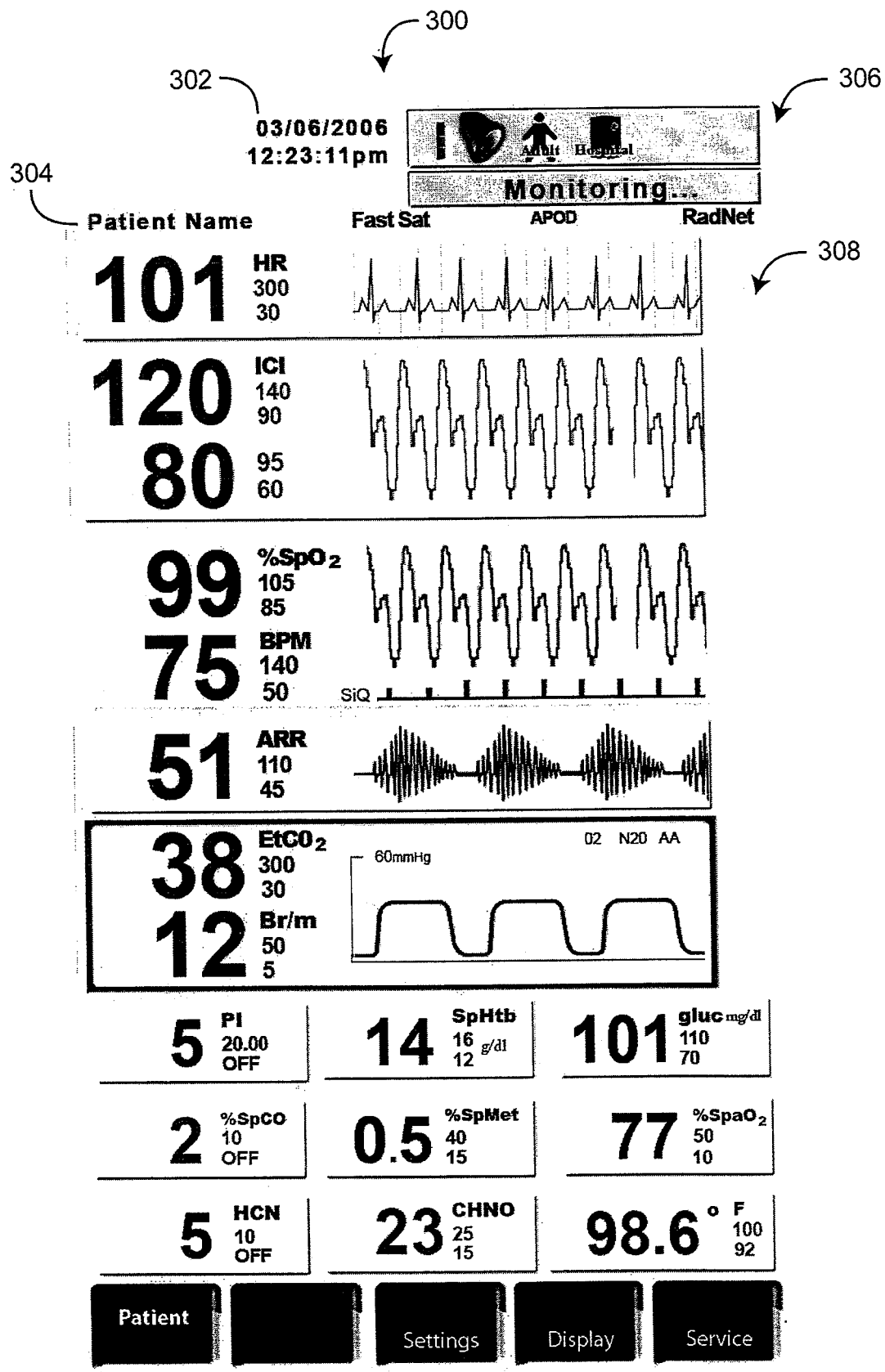
FIG. 3 is a docking station multiple parameter display.

FIG. 3 illustrates a modular patient monitor color display 300. The modular patient monitor display 300 auto-scales its presentation of parameter information based upon the parameters that are active. Fewer parameters result in the display 300 of larger digits and more waveform cycles. In an embodiment, the display 300 has a main menu screen showing date and time 302, patient data 304, battery life and alarm indicators 306 and all enabled parameters 308. Date and time 302 can be enabled or disabled. The display 300 may also have dynamic bar graphs or indicators to show perfusion index and signal quality. Waveforms are displayed for SpO2, NIBP (non-invasive blood pressure), EtCO2 (end-tidal carbon dioxide) and ECG (electrocardiogram) if enabled. Trend waveforms are displayed for parameters that are less dynamic, such as HbCO and HbMet. Further, the display 300 has individual text displays for alarms, alarm suspend, sensor off or no sensor, battery condition, sensitivity, trauma mode, AC power, printer function, recording function, connectivity messages and menus to name a few. Pulse search is indicated by blinking dashes in the pulse and parameter displays. In an embodiment, the color display 300 is an 11.1" LCD with allowance for the use of a 10.4" LCD within the standard mechanical design for the 11.1" display. The docking station 101 also supports any external VGA display.

An exemplar color print illustration of the color display 300 is disclosed in U.S. Provisional Application No. 60/846, 471 entitled Modular Patient Monitor, cited above. In particular, each of the displayed parameters are variously presented in one of a off-white to white shade, lime green to green shade, crimson to red shade, generally turquoise shade, generally chartreuse shade, yellow to gold shade, generally blue and generally purple shade, to name a few.

Figure 4:
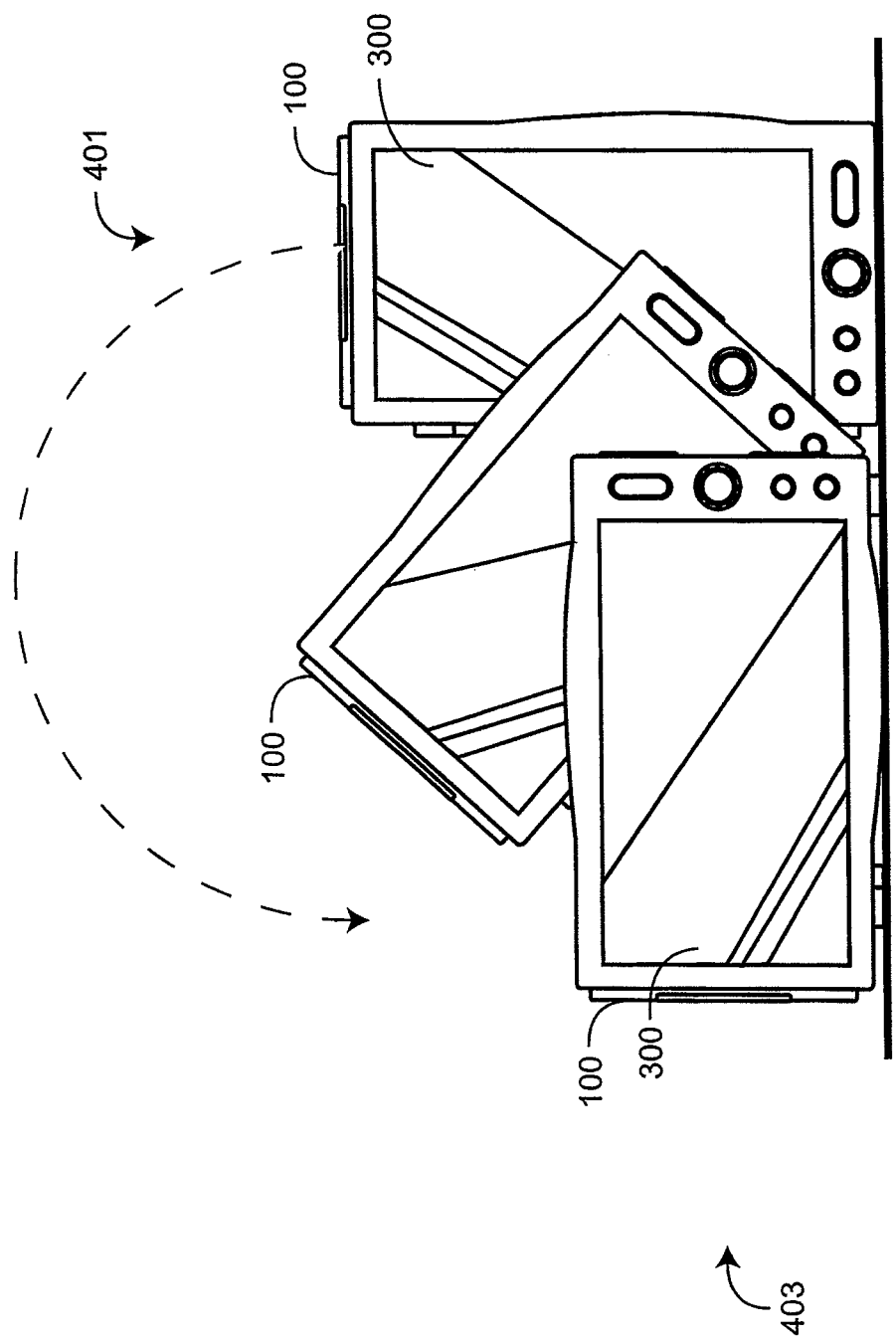
FIG. 4 is an illustration of a modular patient monitor having 90 degree rotation with corresponding display rotation.

FIG. 4 illustrates a modular patient monitor 100 having a vertical orientation 401 and a horizontal orientation 403. In the vertical orientation 401, the display 300 presents data in a vertical format, such as shown in FIG. 3, above. In the horizontal orientation 403, the display 300 presents data in a horizontal format, so that the data appears upright with respect to the viewer. That is, the display 300 automatically switches format according to the patient monitor 100 orientation. A patient monitor having a rotatable display format is described in U.S. Pat. No. 6,770,028 entitled Dual Mode Pulse Oximeter and incorporated by reference herein.

Figure 5A:
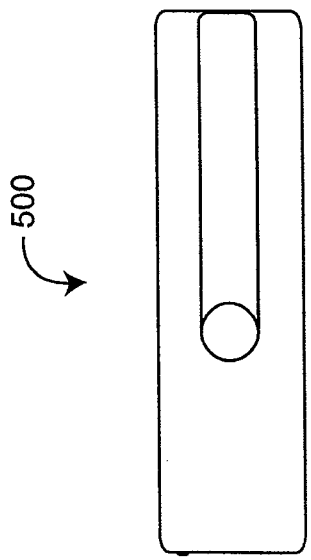
FIGS. 5A-C are top, front and side views of a monitor cartridge.
Figure 5C:
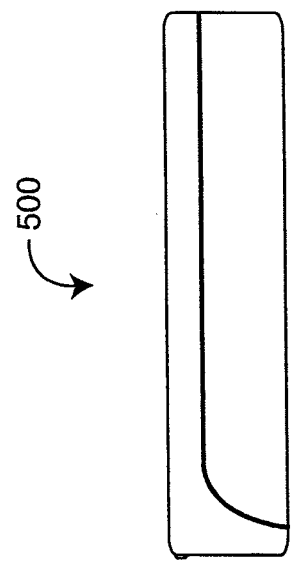
Figure 5B:
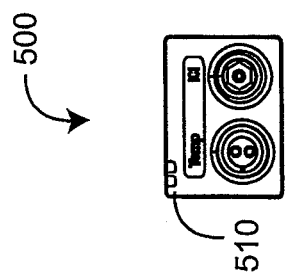

FIGS. 5A-C illustrate an expansion module 500, which the docking station 101 (FIGS. 1A-E) accepts for additional parameters and technologies, such as ICI-NIBP, glucose monitoring, ECG, EtCO2, conscious sedation monitoring, cerebral oximetry, anesthetic agent monitoring, lactate, patient body temperature and assay cartridges, to name a few. The expansion module 500 has an indicator 510 indicating parameters to be provided. In one embodiment, the expansion module 500 provides two parameters to the docking station, which is adapted to accept two modules 500 for four additional parameters. In an embodiment, an ECG module is used to provide an R-wave trigger for ICI-NIBP.

As shown in FIGS. 1A-E, the modular patient monitor 100 includes various connectivity ports 170 such as Ethernet, USB, RS-232, RS-423, nurse call, external VGA and I/O ports for a keyboard and a bar code reader to name a few. As an option, the modular patient monitor 100 has on-board and bedside recorder capability. The modular patient monitor 100 also supports multiple wireless and hardwired communication platforms, web server technology that allows remote viewing of data as well as limited bi-directional control of module functionality and an optional wireless connectivity standards base technology, such as IEEE 802.11x. The wireless option is provided in the handheld 200 and the docking station 101. A wireless module supports the downloading and temporary storage of upgrade software from a remote central server to a destination docking station or a specific module. In an embodiment, the modular patient monitor 100 supports patient context management, specifically the ability to upload or alternatively enter patient unique identification. The modular patient monitor 100 also connects both wired and wirelessly to other patient monitors.

The modular patient monitor 100 may be logged onto via the Internet so as to download raw waveforms and stored trending data for both customer service purposes and for data mining to enhance algorithms and so as to be uploaded with firmware updates. The modular patient monitor 100 may also incorporate removable storage media for the same purpose. In an embodiment, removable storage media functions as a black box, which is a diagnostic tool to retrieve device use information. In particular, the black box can record values displayed, raw waveforms including sounds, and buttons touched by the end user. A patient monitor with removable storage media is described in U.S. patent Ser. No. 10/983,048 entitled Pulse Oximetry Data Capture System filed Nov. 5, 2004 and incorporated by reference herein.

The modular patient monitor 100 may also have an audio module slot (not shown) accommodating an external audio system and wireless headphone module. In an embodiment, the docking station 101 audio system is configured to reproduce respiratory sounds from an ARR (acoustic respiratory rate) sensor.

In an embodiment, the modular patient monitor 100 has a redundant speaker system for alarms. The modular patient monitor 100 may also include alarms for all parameters and a parameter fusion alarm that involves analysis of multiple parameters in parallel. A user can select custom default alarm parameters for adult, pediatric and neonatal patients. A patient monitor having redundant alarm speakers is described in U.S. patent application Ser. No. 11/546,927 entitled Robust Alarm System, filed Oct. 12, 2006 and incorporated by reference herein.

An alarm condition exists for low battery, sensor-off patient, defective sensor, ambient light, parameter limit exceeded and defective speakers, as examples. Audible alarm volume is adjustable and when muted, a visual indicator is illuminated. In an embodiment, the volume is adjustable in at least of four discrete steps. The parameter display flashes to indicate which values are exceeding alarm limits, the parameter is enlarged automatically, and numerics are displayed in either RED or with a RED background. The audible alarm is silence-able with a default alarm silence period for up to two minutes. This delay can be user configurable. Separate from sleep mode, the audible alarms are permanently mutable via a password-protected submenu. The visual alarm indicator still flashes to indicate an alarm condition. A visual indicator on the dashboard indicates an alarm silence condition, such as blinking for temporary silence and solid for muted. An alarm speaker is mounted so as not to be susceptible to muffling from a bed surface, attached external monitor surface or other type of flat resting surface. Redundant and smart alarm annunciation is also provided.

The user accesses the setup menu via a front dashboard knob 140 and mode/enter button 150. TABLE 1 shows user settable parameters. The user can override default settings on a patient-by-patient basis via setup menus.

TABLE 1

| PARAMETER SETTINGS |
| --- |
| SpO$_2$ high & low limit |
| Pulse Rate high & low limit |
| Pulse Tone volume |
| MetHb high and low limit |
| HbCO high & low limit |
| ICI high and low limit |
| tHb high and low limit |
| EtCO$_2$ high and low limit |
| ARR high and low limit |
| Temp high and low limit |
| Glucose high and low limit |
| Audible alarm volume |

Default settings are stored in non-volatile memory (NVM). There is a factory, hospital and user default setting which may be automatically based on patient recognition. The user can choose any of the three at any time. The user may over-write hospital and user default settings with their own preferences via a password protected "save as default" setup menu function. All parameters return to hospital default settings after a power cycle.

In one embodiment, the default settings are as shown in TABLE 2, stored in NVM. These settings are also overwritten into NVM as a result of a factory reset or return to factory defaults function from within the setup menus.

TABLE 2

| PARAMETER | FACTORY DEFAULT |
| --- | --- |
| SpO$_2$ high limit | Off |
| SpO$_2$ low limit | 90 |
| Pulse Rate high limit | 140 |
| Pulse Rate low limit | 40 |
| Alarm Volume | 2 (of 4) |
| Pulse tone volume | 2 (of 4) |
| MetHb high limit | 5% |
| MetHb low limit | Off |
| HbCO high limit | 10% |
| HbCO low limit | Off |
| LCD brightness | 3 (of 5) |

Figure 7A:
FIGS. 7A-C are top, front and side views of an alternative cartridge embodiment.
Figure 7C:
Figure 7B:
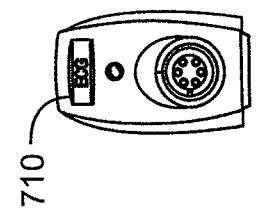

FIGS. 6A-E illustrate another modular patient monitor 600 embodiment having a docking station 601, a handheld monitor 602 and parameter cartridges 700. Each cartridge 700 provides one parameter to the docking station 601, which accepts four cartridges 700 for a total of four additional parameters. Further, the patient monitor 600 also has a cord management channel 630, an oral temperature probe 660 and probe covers 670 located on the docking station 601. The docking station 601 has a trim knob 652 and control buttons 654 on a front stand 653 so as to support system navigation and data entry. The docking station 601 also has a color display 605, a thermal printer 620, an alarm indicator light bar 651, a thermal printer paper door 657 and a handle 659, a sensor holder 655, connectivity ports 680 and a power supply module 690. FIGS. 7A-C illustrate a parameter cartridge 700 having an indicator 710 indicating the parameter or technology provided.

FIGS. 8A-D illustrate a three-piece modular patient monitor 800 including a handheld monitor 810, a shuttle station 830 and a docking station 850. The docking station 850 has a shuttle port 855 that allows the shuttle station 830 to dock. The shuttle station 830 has a handheld port 835 that allows the handheld monitor 810 to dock. Accordingly, the modular patient monitor 800 has three-in-one functionality including a handheld 810, a handheld 810 docked into a shuttle station 830 as a handheld/shuttle 840 and a handheld/shuttle 840 docked into a docking station 850. When docked, the three modules of handheld 810, shuttle 830 and docking station 850 function as one unit.

As shown in FIGS. 8A-D, the handheld module 810 functions independently from the shuttle 830 and docking station 850 and is used as an ultra-light weight transport device with its own battery power. The handheld 810 docked into the shuttle module 830 functions independently of the docking station 850 and expands the handheld parameter capability to the ability to measure all parameters available. The docking station 850, in turn, provides the shuttle 830 or handheld/shuttle 840 with connectivity ports 852, a power supply module 854, a large color display 856, wireless and hardwired communications platforms, a web server and an optional printer. As such, the docking station 850 charges the handheld 810 and shuttle 830, provides a larger screen and controls, such as a trim knob, allows wireless, hardwired and Internet communications and provides connectivity to various external devices. FIG. 8E illustrates another modular patient monitor embodiment 805 having a shuttle 870 with plug-in modules 860 for expanded parameter functionality.

In an embodiment, the handheld monitor 810 incorporates blood parameter measurement technologies including HbCO, HbMet, SpO2 and Hbt, and the shuttle station 830 incorporates non-blood parameters, such as intelligent cuff inflation (ICI), end-tidal CO2 (EtCO2), acoustic respiration rate (ARR), patient body temperature (Temp) and ECG, to name a few. In an alternative embodiment, parameters such as SpO2, ARR and ECG that clinicians need during in-house transports or patient ambulation are loaded into the handheld 810.

Figure 9:
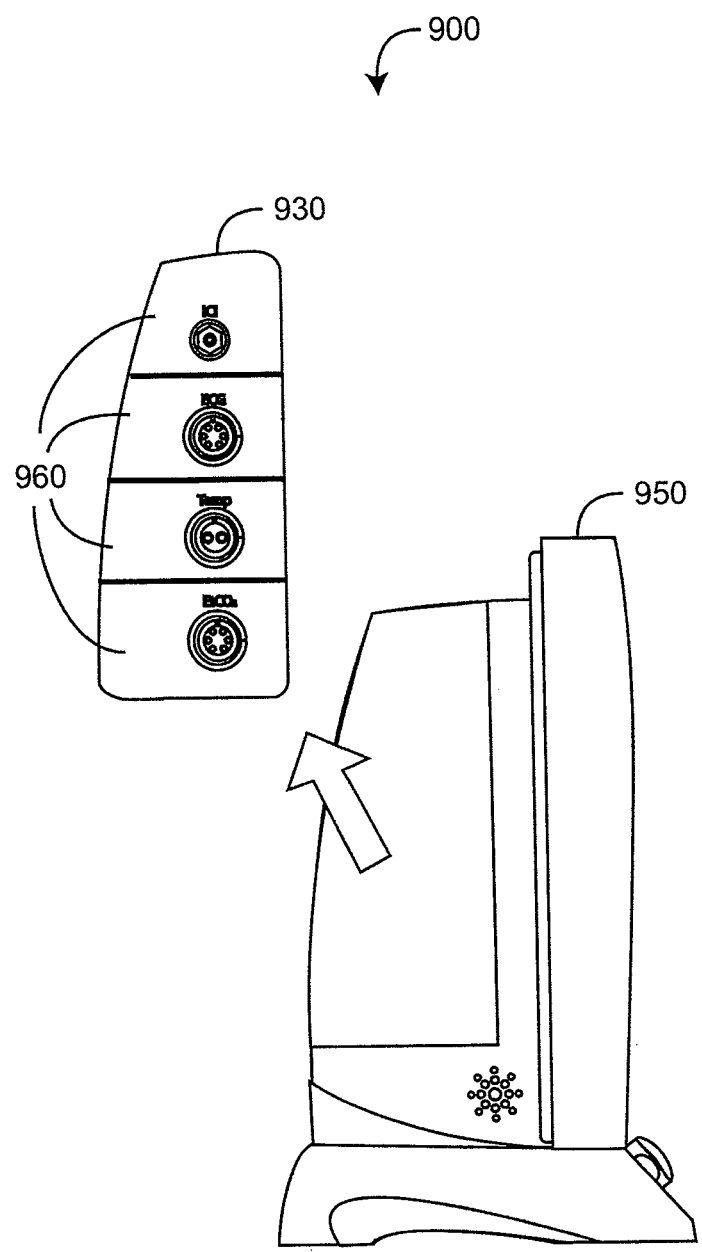
FIG. 9 is a modular patient monitor side view of a further modular patient monitor embodiment having a shuttle without a docking handheld.

FIG. 9 illustrates a two-piece modular patient monitor 900 having a shuttle 930 and a docking station 950 without a corresponding handheld. In an embodiment, the shuttle 930 has plug-in modules 960 for added parameter functions.

FIGS. 10A-C illustrate yet another modular patient monitor 1000 embodiment having dual removable handhelds 1010 and a docking station 1050 without a corresponding shuttle. For example, the handhelds 1010 may include one blood parameter monitor and one non-blood parameter monitor.

Figure 13B:
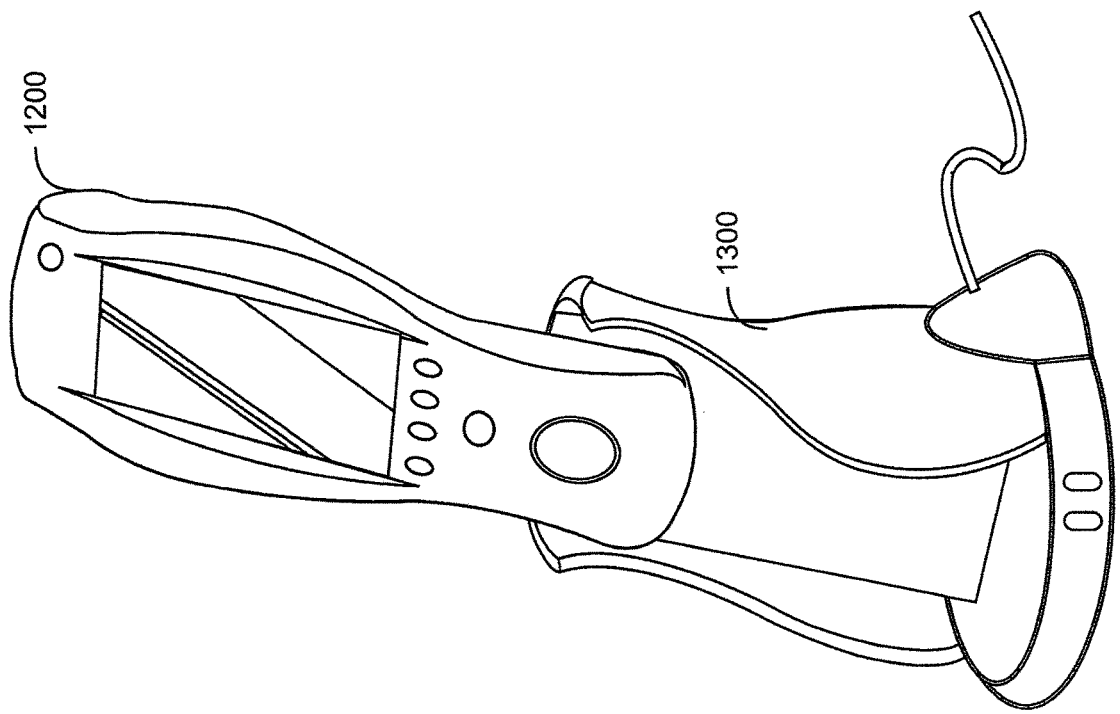
FIGS. 13A-B are front perspective views of an alternative handheld embodiment plugged into, and removed from, a charger.
Figure 13A:
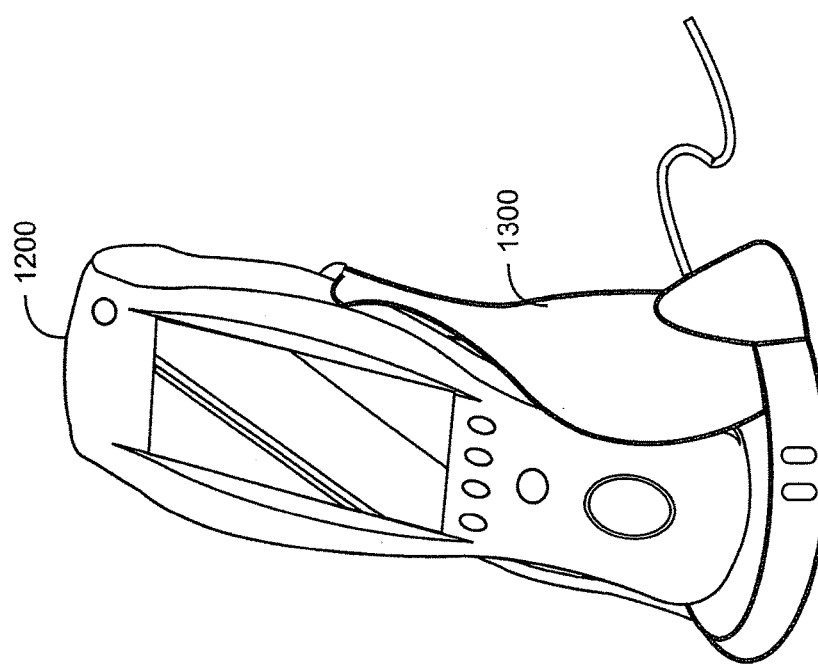

FIGS. 11A-C illustrate a handheld tablet monitor 1100 having a display 1110, a trim knob 1120 and control buttons 1130. An electroluminescent lamp 1140 on the front panel provides a thin uniform lighting with low power consumption. A temperature probe 1150 is attached to the monitor 1100. The tablet monitor 1100 connects to a multiple parameter sensor through a patient cable 1160. FIGS. 12-13 illustrate a handheld monitor 1200 configured to plug into a compact holder/battery charger 1300. The handheld monitor 1200 is adapted to plug into the compact charger 1300.

Figure 14:
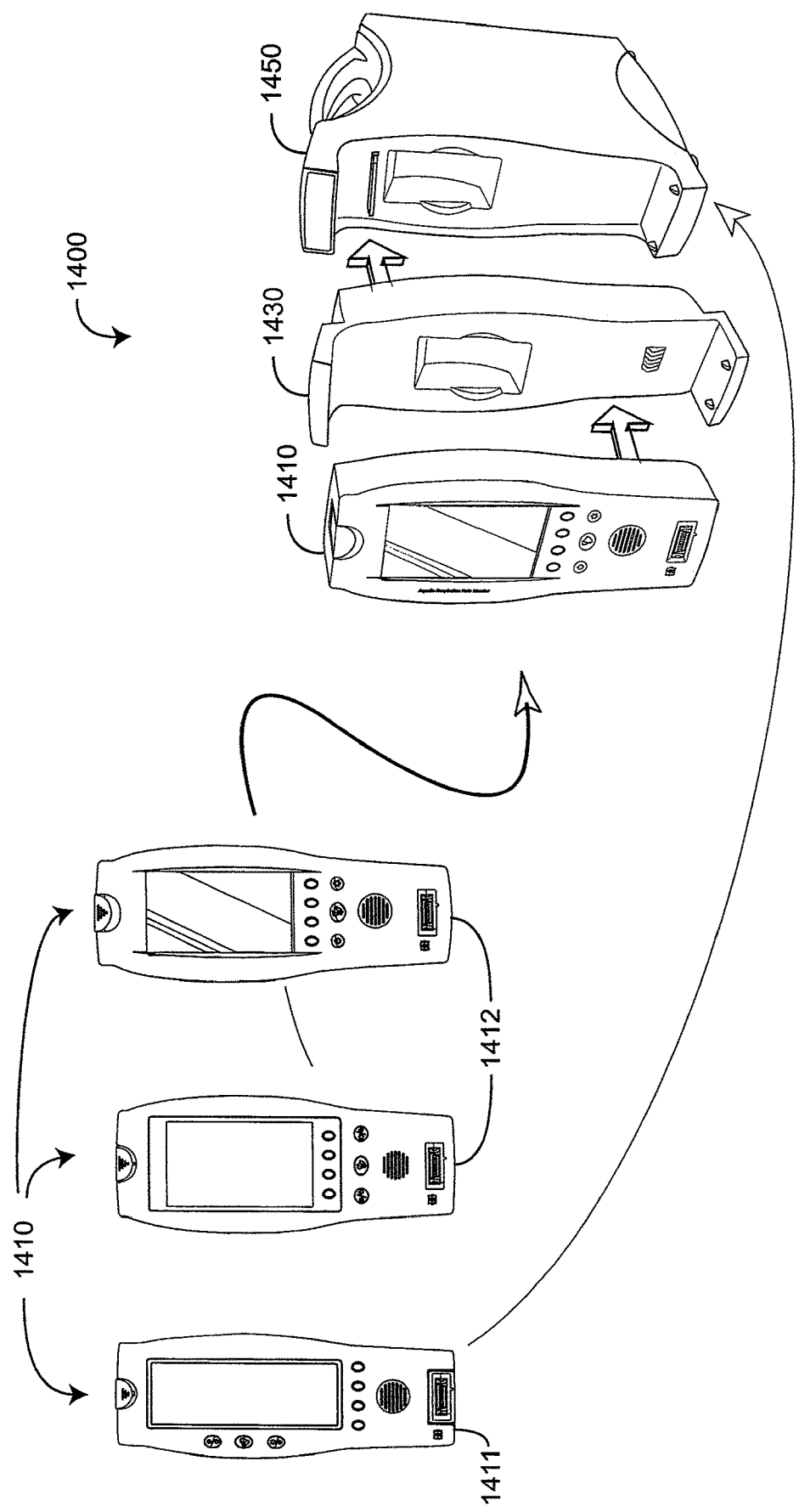
FIG. 14 is a perspective view of upgrade and legacy handhelds installable into a legacy docking station directly or via a docking station adapter.

FIG. 14 illustrates a modular patient monitor 1400 embodiment having various handheld monitors 1410, a docking station adapter 1430 and a legacy docking station 1450. The handheld monitors 1410 can include legacy handhelds 1411 and upgrade handhelds 1412. The docking station adapter 1430 is configured for the legacy docking station 1450 so that both legacy handhelds 1411 and upgrade handhelds 1412 can dock into the legacy docking station 1450 directly or via the docking station adapter 1430.

Figure 15A:
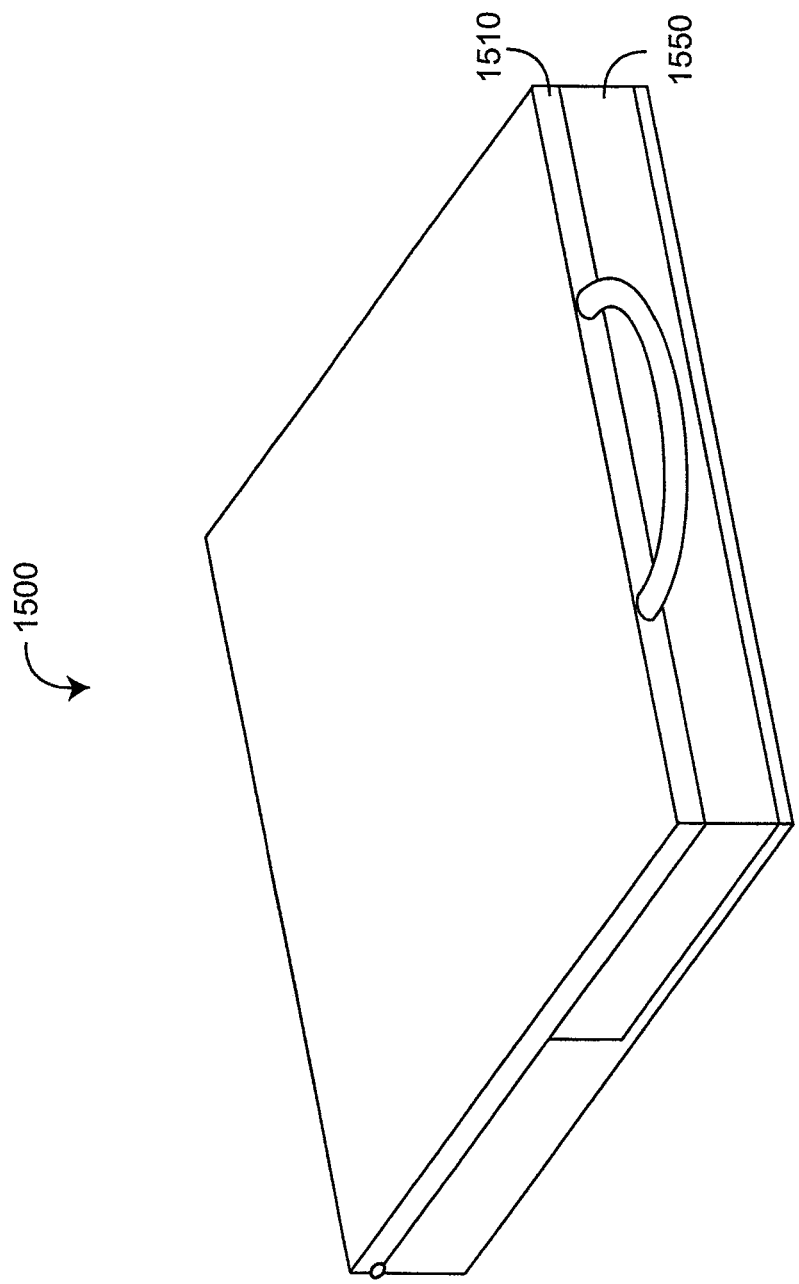
FIGS. 15A-B are closed and opened views, respectively, of a notebook-style modular patient monitor embodiment having a foldable display.
Figure 15B:
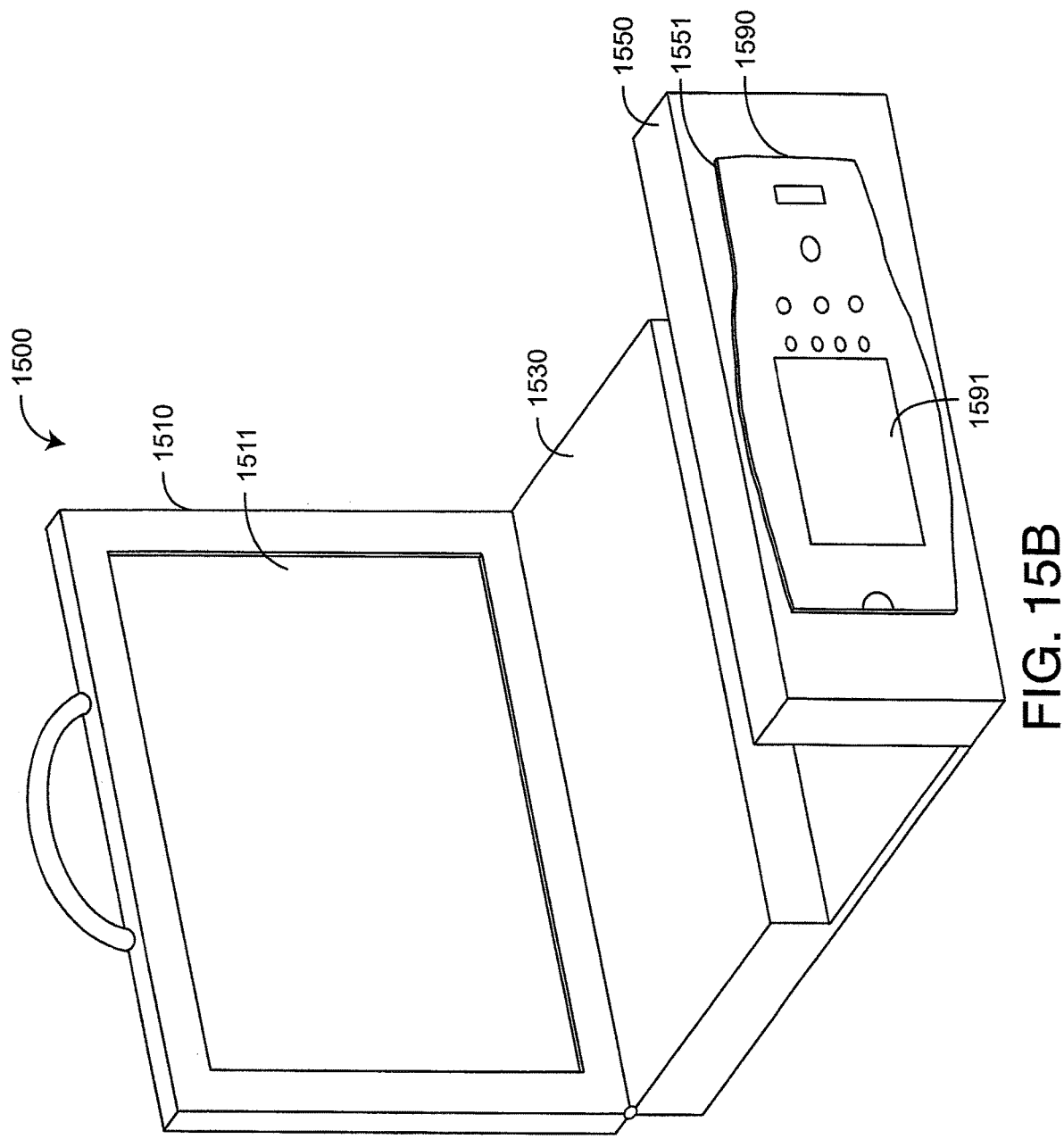

FIGS. 15A-B illustrate a "notebook" modular patient monitor 1500 embodiment having a foldable lid 1510, a fixed body 1530 and a foldable docking station 1550. The fixed body 1530 houses patient monitor electronics and provides external device connectivity at a back end (not visible). The lid 1510 has a notebook display 1551, such as a color LCD. The docking station 1550 has a port 1551 that removably connects, both mechanically and electrically, a corresponding handheld monitor 1590, such as the handheld embodiments described above. In a closed position (FIG. 15A), the notebook monitor 1500 can be carried via an optional handle or simply in hand or under an arm. In an open position (FIG. 15B), the notebook monitor is operational, connecting to patient sensors via the handheld 1590 or a sensor connector (not shown) on the back end of the notebook. In the open position, the docking station 1550 can stay in a stowed or folded position (not shown) so that the handheld screen 1591 faces upward. Alternatively, in the open position, the docking station 1500 is unfolded as shown (FIG. 15B) so that the handheld display 1591 can be easily viewed from the front of the notebook in conjunction with the notebook display 1511 in the lid 1510. In an embodiment, the notebook 1550 can have a conventional keyboard and touch pad, have conventional monitor controls, incorporate a conventional computer and peripherals or a combination of the above. As shown, the notebook display 1511 faces inward, so that the display 1511 is protected in the folded position. In another embodiment, the display 1511 faces outward (not shown).

Figure 16:
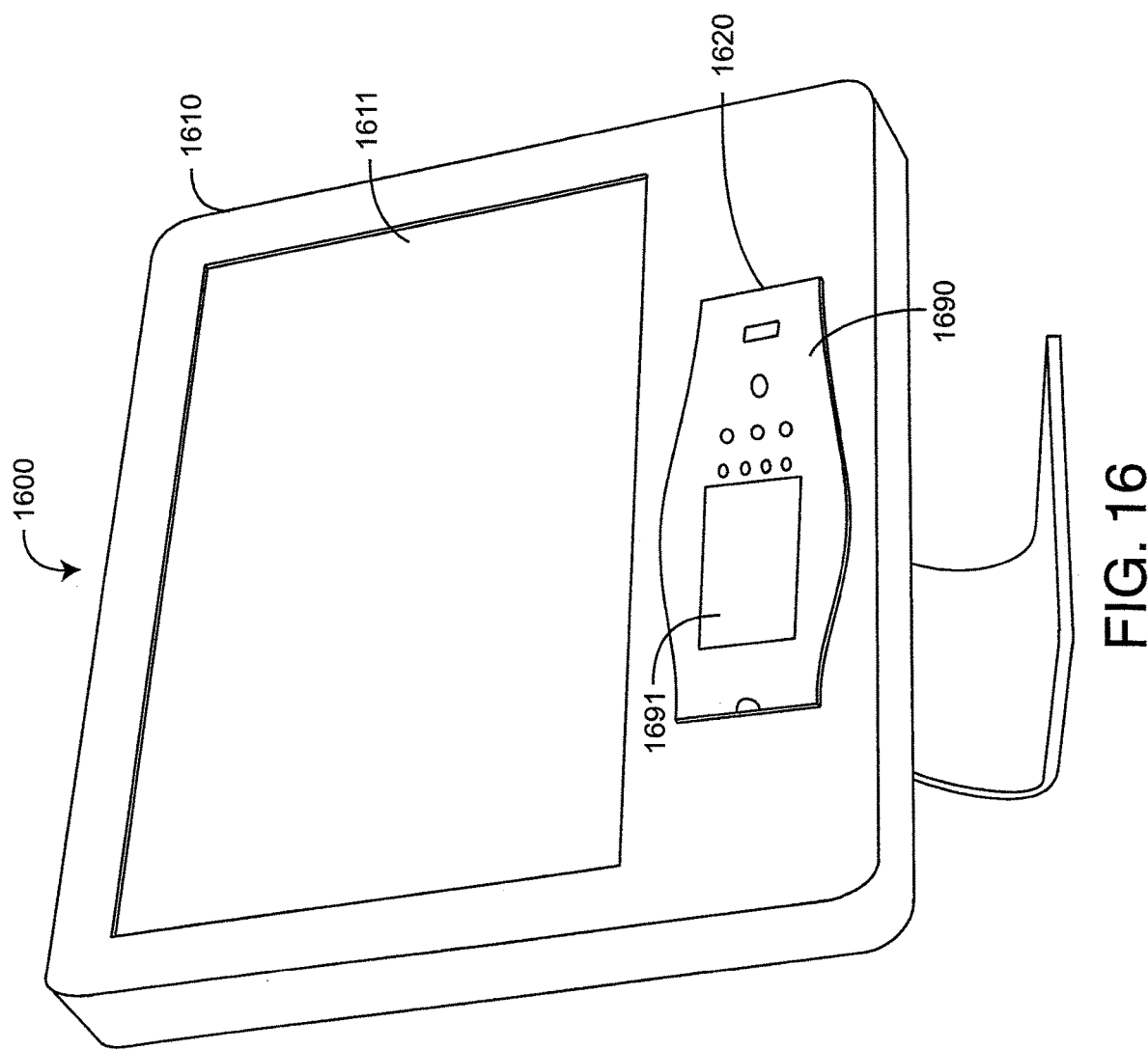
FIG. 16 is a perspective view of a flat panel display docking station.

FIG. 16 illustrates a flat panel modular patient monitor embodiment 1600 having a flat panel body 1610 housing a flat panel display 1611 and a handheld port 1620. The handheld port 1620 removably accepts a handheld monitor 1690 having a handheld display 1691, such as the handheld monitors described above. The flat panel monitor 1600 can be free-standing on a table top, wall-mounted or mounted on or integrated within a patient bed, as a few examples. The flat panel monitor 1600 can be simply a docking and display device or can provide built-in patient monitoring functions and parameters not available to the handheld 1690.

A modular patient monitor has been disclosed in detail in connection with various embodiments. These embodiments are disclosed by way of examples only and are not to limit the scope of the claims that follow. One of ordinary skill in art will appreciate many variations and modifications.

What is claimed is:
1. A patient monitoring system comprising:
a docking station including a housing, a first display integrated with the docking station, a shuttle port, and a processor configured to:
receive physiological signals responsive to a first set of physiological parameters of a patient from one or more physiological sensors,
calculate measurements of the first set of physiological parameters based on the physiological signals,
cause at least some measurements of the first set of physiological parameters to be displayed on the first display, automatically determine a number of physiological parameters that are active for measurements to be displayed on the first display, auto-scale measurements displayed on the first display based at least in part on the determined number of physiological parameters that are active for measurements to be displayed on the first display, wherein measurements are automatically displayed larger on the first display when fewer physiological parameters are active for measurements to be displayed on the first display;

a shuttle station removably attachable to the docking station via the shuttle port and including a handheld port; and a handheld monitor removably attachable to the shuttle station via the handheld port and including a second display integrated with the handheld monitor and a processor configured to:

receive physiological signals responsive to a second set of physiological parameters of the patient, at least some of the physiological signals output from a noninvasive sensor and responsive to light attenuated by blood, calculate measurements of the second set of physiological parameters based on the physiological signals, and cause at least some measurements of the second set of physiological parameters to be displayed on the second display, wherein in a docked configuration in which the handheld monitor is docked to the handheld port of the shuttle station, and the shuttle station is docked to the shuttle port of the docking station:

at least one of the processor of the handheld monitor or the processor of the docking station is configured to cause at least some measurements of a combination of the first and second sets of physiological parameters to be displayed on the first display, and the docking station is configured to electrically charge the handheld monitor via the shuttle station, and wherein in a second docked configuration in which the handheld monitor is docked to the handheld port of the shuttle station, and the shuttle station is not docked to the shuttle port of the docking station:

the shuttle station and the handheld monitor function together independently of the docking station, and the shuttle station provides expanded parameter capability to the handheld monitor.

2. The patient monitoring system of claim 1, wherein the first display occupies substantially all of a display side of the housing.

3. The patient monitoring system of claim 1, wherein at least some of the measurements of the first set of physiological parameters are different from at least some of the measurements of the second set of physiological parameters.

4. The patient monitoring system of claim 1, wherein the at least some measurements of the combination of the first and second sets of physiological parameters include at least some measurements of the first set of physiological parameters and at least some measurements of the second set of physiological parameters.

5. The patient monitoring system of claim 1, wherein:
the first set of physiological parameters comprises a non-blood constituent; and
the second set of physiological parameters comprises a blood constituent.

6. The patient monitoring system of claim 1 further comprising:
an expansion module,
wherein said shuttle station further includes a module port, wherein when the expansion module is docked in the module port, the shuttle station adds a capability of measuring at least one additional physiological parameter.

7. The patient monitoring system of claim 1, wherein a display size of the first display is substantially larger than a display size of the second display.

8. The patient monitoring system of claim 1, wherein in the docked configuration, the number of physiological parameters that are active for measurements to be displayed on the first display include the at least some measurements of the combination of the first and second sets of physiological parameters to be displayed on the first display.

9. The patient monitoring system of claim 1, wherein the shuttle station includes plug-in modules for the expanded parameter capability.

10. A method of displaying measurements of physiological parameters, the method comprising:

receiving, at a docking station, from one or more physiological sensors, first physiological signals responsive to a first set of physiological parameters of a patient, the docking station including a housing, a first display, a shuttle port, and a first processor;

calculating, by the first processor, measurements of the first set of physiological parameters based on the first physiological signals;

causing, by the first processor, at least some measurements of the first set of physiological parameters to be displayed on the first display;

automatically determine, by the first processor, a number of physiological parameters that are active for measurements to be displayed on the first display, auto-scale, by the first processor, measurements displayed on the first display based at least in part on the determined number of physiological parameters that are active for measurements to be displayed on the first display, wherein measurements are automatically displayed larger on the first display when fewer physiological parameters are active for measurements to be displayed on the first display;

receiving, at a handled monitor, second physiological signals responsive to a second set of physiological parameters of the patient, at least some of the second physiological signals output from a noninvasive sensor and responsive to light attenuated by blood, wherein the handheld monitor is removably attachable to a shuttle station via a handheld port of the shuttle station and includes a second processor and a second display integrated with the handheld monitor, and wherein the shuttle station is removably attachable to the docking station via the shuttle port and includes the handheld port;

calculating, by the second processor, measurements of a second set of physiological parameters based on the second physiological signals;

causing, by the second processor, at least some measurements of the second set of physiological parameters to be displayed on the second display;

in a docked configuration in which the handheld monitor is docked to the handheld port of the shuttle station, and the shuttle station is docked to the shuttle port of the docking station:

causing, by at least one of the first and second processors, at least some measurements of a combination of the first and second sets of physiological parameters to be displayed on the first display; and causing, by at least one of the first and second processors, the docking station to electrically charge the handheld monitor via the shuttle station; and in a second docked configuration in which the handheld monitor is docked to the handheld port of the shuttle station, and the shuttle station is not docked to the shuttle port of the docking station:

causing, by at least the second processor, the shuttle station and the handheld monitor to function together independently of the docking station, wherein the shuttle station provides expanded parameter capability to the handheld monitor.

11. The method of claim 10, wherein the first display occupies substantially all of a display side of the housing.

12. The method of claim 10, wherein at least some of the measurements of the first set of physiological parameters are different from at least some of the measurements of the second set of physiological parameters.

13. The method of claim 10, wherein the at least some measurements of the combination of the first and second sets of physiological parameters includes at least some measurements of the first set of physiological parameters and at least some measurements of the second set of physiological parameters.

14. The method of claim 10, wherein:

the first set of physiological parameters comprises a non-blood constituent; and the second set of physiological parameters comprises a blood constituent.

15. The method of claim 10 further comprising:

providing an expansion module, wherein said shuttle station further includes a module port, wherein when the expansion module is docked in the module port, the shuttle station adds a capability of measuring at least one additional physiological parameter.

16. The method of claim 10, wherein a display size of the first display is substantially larger than a display size of the second display.

17. The method of claim 10, wherein in the docked configuration, the number of physiological parameters that are active for measurements to be displayed on the first display include the at least some measurements of the combination of the first and second sets of physiological parameters to be displayed on the first display.

18. The method of claim 10, wherein the shuttle station includes plug-in modules for the expanded parameter capability.

* * * * *